US009616358B2

(12) United States Patent
Hembre et al.

(10) Patent No.: US 9,616,358 B2
(45) Date of Patent: *Apr. 11, 2017

(54) QUATERNARY PHOSPHINATES WITH CO-SOLVENTS FOR EXTRACTING $C_1$ TO $C_4$ CARBOXYLIC ACIDS FROM AQUEOUS STREAMS

(71) Applicant: Eastman Chemical Company, Kingsport, TN (US)

(72) Inventors: Robert Thomas Hembre, Johnson City, TN (US); Scott Donald Barnicki, Kingsport, TN (US); Chester Wayne Sink, Kingsport, TN (US); Christopher Hardacre, Belfast (GB)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/973,817

(22) Filed: Dec. 18, 2015

(65) Prior Publication Data

US 2016/0175738 A1 Jun. 23, 2016

Related U.S. Application Data

(60) Provisional application No. 62/094,238, filed on Dec. 19, 2014.

(51) Int. Cl.
| | | |
|---|---|---|
| *B01D 11/04* | (2006.01) | |
| *C07C 51/44* | (2006.01) | |
| *C07C 51/48* | (2006.01) | |
| *C07F 9/54* | (2006.01) | |
| *C07F 9/30* | (2006.01) | |

(52) U.S. Cl.
CPC .......... *B01D 11/0492* (2013.01); *C07C 51/44* (2013.01); *C07C 51/48* (2013.01); *C07F 9/301* (2013.01); *C07F 9/5407* (2013.01); *Y02P 20/542* (2015.11)

(58) Field of Classification Search
CPC ..... B01D 11/0492; C07C 51/44; C07C 51/48; C07F 9/5407; C07F 9/301; Y02P 51/48
See application file for complete search history.

(56) References Cited

U.S. PATENT DOCUMENTS

| | | |
|---|---|---|
| 1,839,894 A | 1/1932 | Ricard et al. |
| 1,860,512 A | 5/1932 | Ricard et al. |
| 1,861,841 A | 6/1932 | Clarke et al. |
| 1,917,391 A | 7/1933 | Othmer |
| 2,028,800 A | 1/1936 | Othmer |
| 2,050,234 A | 8/1936 | Othmer |
| 2,063,940 A | 12/1936 | Martin |
| 2,076,184 A | 4/1937 | Othmer |
| 2,123,348 A | 7/1938 | Wentworth |
| 2,157,143 A | 5/1939 | Othmer |
| 2,184,563 A | 12/1939 | Othmer |
| 2,199,983 A | 5/1940 | Bright |
| 2,204,616 A | 6/1940 | Othmer |
| 2,269,163 A | 1/1942 | Othmer |
| 2,275,802 A | 3/1942 | Othmer |
| 2,275,862 A | 3/1942 | Othmer |
| 2,317,758 A | 4/1943 | Guinot |
| 2,333,756 A | 11/1943 | Wentworth |
| 2,384,374 A | 9/1945 | Harrison |
| 2,395,010 A | 2/1946 | Othmer |
| 2,537,658 A | 1/1951 | Dornte |
| 2,567,244 A | 9/1951 | Solomon |
| 2,854,385 A | 9/1958 | Alheritiere |
| 2,859,154 A | 11/1958 | Othmer |
| 3,052,610 A | 9/1962 | Akaboshi et al. |
| 3,816,524 A | 6/1974 | Grindstead |
| 4,909,939 A | 3/1990 | Rickelton |
| 5,662,780 A | 9/1997 | Sasaki et al. |
| 5,663,422 A | 9/1997 | Perri et al. |
| 7,435,318 B2 | 10/2008 | Arlt et al. |
| 7,709,168 B2 | 5/2010 | Wu et al. |
| 7,812,191 B2 | 10/2010 | Hallinan et al. |
| 7,858,678 B2 | 12/2010 | Avakian et al. |
| 8,540,900 B2 | 9/2013 | Foley et al. |
| 8,674,050 B2 | 3/2014 | Spyrou |
| 2012/0138789 A1 | 6/2012 | Del Sesto et al. |
| 2014/0076805 A1 | 3/2014 | Massingill |
| 2014/0275597 A1 | 9/2014 | Zhang et al. |

FOREIGN PATENT DOCUMENTS

| | | |
|---|---|---|
| DE | 3035641 A1 | 5/1982 |
| EP | 1 645 577 A1 | 4/2006 |
| EP | 2 530 066 A1 | 12/2012 |
| JP | 2014-40389 A | 3/2014 |
| WO | 02/079212 A1 | 10/2002 |
| WO | 03/020843 A1 | 3/2003 |
| WO | 2006/007703 A1 | 1/2006 |
| WO | 2014/060651 A1 | 4/2014 |

OTHER PUBLICATIONS

A. Stojanovic et al., "Phosphonium and Ammonium Ionic Liquids with Aromatic Anions: Synthesis, Properties, and Platinum Extraction," Aust. J. Chem., vol. 63, pp. 511-524 (2010).
G. Cui et al., "Tuning Anion-Functionalized Ionic Liquids for Improved SO2 Capture," Agnew. Chem. Int. Ed., vol. 52, pp. 10620-10624 (2013).
G. Cui et al., "Tuning the Basicity of Cyano-Containing Ionic Liquids to Improve SO2 Capture through Cyano-Sulfur Interactions," Chem. Eur. J., vol. 21, pp. 5632-5639 (2015).
(Continued)

*Primary Examiner* — Shailendra Kumar
(74) *Attorney, Agent, or Firm* — Phan Law Group PLLC

(57) ABSTRACT

This invention relates to solvents for extracting $C_1$ to $C_4$ carboxylic acids from aqueous streams. More specifically, the extraction solvents include one or more salts composed of a tetraalkylphosphonium cation and a phosphinate anion. The extraction solvents may further include one or more co-solvents as an enhancer. The co-solvents may be selected from higher carboxylic acids, ethers, esters, ketones, aromatic hydrocarbons, chlorinated hydrocarbons, and nitriles. The extraction solvents are useful for extracting aqueous mixtures containing one or more lower carboxylic acids, such as monocarboxylic acids and organofluorine carboxylic acids.

30 Claims, No Drawings

(56) References Cited

OTHER PUBLICATIONS

S. Das et al., "Ionic liquid-based fluorescien colorimetric pH nanosensors," RSC Adv., vol. 3, pp. 21054-21061 (2013).

S. Murugesan et al., "Benzoate-based room temperature ionic liquids—thermal properties and glycosaminoglycan dissolution," Carbohydrate Polymers, vol. 63, pp. 268-271 (2006).

J. McFarlane et al., "Room Temperature Ionic Liquids for Separating Organics from Produced Water," Separation Sci. and Tech., vol. 40, pp. 1245-1265 (2005).

Int'l Search Report and Written Opinion issued in Int'l Application No. PCT/US2015/066575, 2016.

Q. Yang et al., "Long-Chain Fatty Acid-Based Phosphonium Ionic Liquids with Strong Hydrogen-Bond Basicity and Good Lipophilicity: Synthesis, Characterization, and Application in Extraction," ACS Sustainable Chem. Eng., vol. 3, pp. 309-316 (2015).

K. Park et al., "Ionic Liquids as Plasticizers/Lubricants for Polylactic Acid," Polymer Eng. and Sci., vol. 50, pp. 1105-1110 (2009).

A. Rosatella et al., "Studies on dissolution of carbohydrates in ionic liquids and extraction from aqueous phase," Green Chem., vol. 11, pp. 1406-1413 (2009).

M. Selva et al., "Carbonate, acetate and phenolate phosphonium salts as catalysts in transesterification reactions for the synthesis of non-symmetric dialkyl carbonates," Org. Biomol. Chem., vol. 10, pp. 6569-6578 (2012).

V. Shaturin et al., "Tetraphenylphosphonium Carboxylates and Sulfonates. Synthesis and Structure," Russian J. Gen. Chem., vol. 79, pp. 78-87 (2009).

A. Holding et al., "Amphiphilic and Phase-Separable Ionic Liquids for Biomass Processing," ChemSusChem, vol. 7, pp. 1422-1434 (2014).

M. Blesic et al., "Solubility of alkanes, alkanols and their fluorinated counterparts in tetraalkylphosphonium ionic liquids," Phys. Chem. Chem. Phys., vol. 12, pp. 9685-9692 (2010).

Y. Zhou et al., "Ionic Liquids Composed of Phosphonium Cations and Organophosphate, Carboxylate, and Sulfonate Anions as Lubricant Antiwear Additives," Langmuir, vol. 30, pp. 13301-13311 (2014).

C. Neves et al., "Separation of ethanol-water mixtures by liquid-liquid extraction using phosphonium-based ionic liquids," Green Chem., vol. 13, pp. 1517-1526 (2011).

F. Vicente et al., "Design of novel aqueous micellar two-phase systems using ionic liquids as co-surfactants for the selective extraction of (bio)molecules," Sep. and Purif. Tech., vol. 135, pp. 259-267 (2014).

A. Grijalba et al., "Capabilities of several phosphonium ionic liquids for arsenic species determination in water by liquid-liquid microextraction and electrothermal atomic absorption spectrometry," Anal. Methods, vol. 7, pp. 490-499 (2015).

P. Dallas et al., "Self-suspended permanent magnet FePt ferrofluids," J. Colloid and Interface Sci., vol. 407, pp. 1-7 (2013).

G. Yadav et al., "Ionic Liquid as Catalyst for Solid-Liquid Phase Transfer Catalyzed Synthesis of p-Nitrodiphenyl Ether," Ind. Eng. Chem. Res., vol. 47, pp. 9081-9089 (2008).

F. Oliveira et al., "Extraction of I-lactic,I-malic, and succinic acids using phosphonium-based ionic liquids," Sep. and Purif. Tech., vol. 85, pp. 137-146 (2012).

Int'l Search Report and Written Opinion issued in Int'l Application No. PCT/US2015/066571; 2016.

J. Martak et al., "Phosphonuim Ionic Liquids as New, Reactive Extractants of Lactic Acid," Chem. Papers, vol. 60, pp. 395-398 (2006).

M. Blahusiak et al., "New approach to regeneration of an ionic liquid containing solvent by molecular distillation," Chem. Papers, vol. 65, pp. 603-607 (2011).

Y. Jiang et al., "Enzymatic Hydrolysis of Penicillin for 6-APA Production in Three-Liquid-Phase System," Applied Biochem. Biotech., vol. 144, pp. 145-159 (2008).

G. Nemeth et al., "Asymmetric lactic acid esterification with biocatalysts in ionic liquid," Hungarian J. Indus. Chem., vol. 39, pp. 419-425 (2011).

B. Major et al., "Microwave assisted enzymatic esterification of lactic acid and ethanol in phosphonium type ionic liquids as co-solvents," Green Chem., vol. 11, pp. 614-616 (2009).

Int'l Search Report and Written Opinion issued in Int'l Application No. PCT/US2015/066572, 2016.

Hembre et al., Copending U.S. Appl. No. 14/973,812, filed Dec. 18, 2015.

Liu et al., Copending U.S. Appl. No. 14/973,826, filed Dec. 18, 2015.

Eaglesfield et al., "Recovery of Acetic Acid from Dilute Aqueous Solutions by Liquid-Liquid Extraction—Part 1," The Industrial Chemist, vol. 29, pp. 147-151 (1953).

King, "Amine-Based Systems for Carboxylic Acid Recovery: Tertiary Amines and the Proper Choice of Diluent Allow Extraction and Recovery from Water," ChemTech, vol. 5, pp. 285-291 (1992).

Tamada et al., "Extraction of Carboxylic Acids with Amine Extractants. 2. Chemical Interactions and Interpretation of Data," Ind. Eng. Chem. Res., vol. 29, pp. 1327-1333 (1990).

Blahusiak et al., "Extraction of butyric acid with a solvent containing ammonium ionic liquid," Sep. Purif. Technol., vol. 119, pp. 102-111 (2013).

Poole et al., "Extraction of Organic Compounds with Room Temperature Ionic Liquids," J. Chromatogr. (A), vol. 1217, pp. 2268-2286 (2010).

Bradaric et al., "Industrial Preparation of Phosphonium Ionic Liquids", Green Chem., vol. 5, pp. 143-152 (2003).

Matsumoto et al., "Extraction of Organic Acids Using Imidazolium-Based Ionic Liquids and Their Toxicity to Lactobacillus rhamnosus," Sep. Purif. Technol., vol. 40, pp. 97-101 (2004).

Cieniecka-Roslonkiewicz et al., "Synthesis, anti-microbial activities and anti-electrostatic properties of phosphonium-based ionic liquids," Green Chem., vol. 7, pp. 855-862 (2005).

Kogelnig et al., "Greener Synthesis of New Ammonium Ionic Liquids and their Potential as Extracting Agents," Tetrahedron Letters, vol. 49, pp. 2782-2785 (2008).

Ferguson et al., "A Greener, Halide-Free Approach to Ionic Liquid Synthesis," Pure & Appl. Chem., vol. 84, pp. 723-744 (2012).

Wardell et al., "Solvent Equilibria for Extraction of Carboxylic Acids from Water," J. Chem. Eng. Data, vol. 23, No. 2, pp. 144-148 (1978).

Rocha et al., "Extraction of Volatile Fatty Acids Using Nature Based Ionic Liquids," Proceedings of the 20th European Conference on Thermophysical Properties (ECTP), Aug. 31-Sep. 4, Porto, Portugal, pp. 1-7 (2014).

Martak et al., "Ionic Liquids in Pertraction and Extraction of Organic Acids," XIX-th Ars Separatoria, Zloty Potok, Poland, pp. 106-113 (2004).

Martak et al., "Screening of ionic liquids for application in solvent extraction and pertration," 31th Int'l Conf. SSCHE, Tatranske Matliare, Slovakia, p. 188 (2004).

Martak et al., "Liquid-liquid equilibria of butyric acid for solvents containing a phosphonium ionic liquid," Chem. Papers, vol. 62, pp. 42-50 (2008).

Martak et al., "Extraction of Lactic Acid by Phosphonium Ionic Liquids," Sep. Purif. Technol., vol. 57, pp. 483-494 (2007).

QUATERNARY PHOSPHINATES WITH CO-SOLVENTS FOR EXTRACTING $C_1$ TO $C_4$ CARBOXYLIC ACIDS FROM AQUEOUS STREAMS

CROSS-REFERENCE TO RELATED APPLICATION

This application claims the benefit of Provisional Application No. 62/094,238 filed on Dec. 19, 2014 under 35 U.S.C. §119(e)(1); the entire content of the provisional application is hereby incorporated by reference.

FIELD OF THE INVENTION

The invention generally relates to solvents for extracting $C_1$ to $C_4$ carboxylic acids from aqueous streams, compositions containing the same, and processes for separating the acids from water.

BACKGROUND OF THE INVENTION

The recovery of $C_1$ to $C_4$ carboxylic acids (hereinafter "lower acids") from aqueous streams is a common industrial problem arising from a variety of reaction and processing steps. Simple distillation of wet acid streams to recover glacial acids is hampered by unfavorable vapor-liquid equilibrium (VLE) and high energy costs with all $C_1$ to $C_4$ carboxylic acids. Examples of unfavorable VLE include the formic acid-water maximum-boiling homogeneous azeotrope, the acetic acid-water VLE "pinch" (a region of low relative volatility), and the minimum-boiling homogeneous azeotropes with water and all $C_3$-$C_4$ carboxylic acids.

Various approaches have been suggested in the art to address the problem of lower acid recovery from wet acid feeds. For example, one approach subjects an aqueous lower acid solution to azeotropic distillation together with an entraining component capable of forming a heterogeneous minimum-boiling azeotrope with water, so that the azeotrope boils at a temperature substantially lower than pure water, the pure lower acid, and any acid-water azeotrope. An extraction step often precedes the azeotropic distillation. The extraction step partitions the carboxylic acid into a water-immiscible solvent (which is often the same as the azeotropic entrainer) in order to remove the bulk of the water from the recovered acid. Many examples of azeotropic distillation, extraction, and combinations thereof using conventional organic solvents have been proposed in the art. These include U.S. Pat. Nos. 1,839,894; 1,860,512; 1,861,841; 1,917,391; 2,028,800; 2,050,234; 2,063,940; 2,076,184; 2,123,348; 2,157,143; 2,184,563; 2,199,983; 2,204,616; 2,269,163; 2,275,834; 2,275,862; 2,275,867; 2,317,758; 2,333,756; 2,359,154; 2,384,374; 2,395,010; 2,537,658; 2,567,244; 2,854,385; 3,052,610; and 5,662,780, and Eaglesfield et al., "Recovery of Acetic Acid from Dilute Aqueous Solutions by Liquid-Liquid Extraction—Part 1," *The Industrial Chemist*, Vol. 29, pp. 147-151 (1953).

Several solvent characteristics determine the capital and energy costs of extraction-distillation processes for the extractive recovery of lower acids from wet acid feeds. The solvent for the extraction process is immiscible with water and meets two criteria:

a) The solvent shows some selectivity between extraction of the carboxylic acid and water, i.e., the ratio of carboxylic acid to water in the extraction solvent after extraction is substantially larger than in the wet acid feed stream. This factor can be quantified as the weight ratio of water to acid in the extract stream as defined in more detail below.

b) The solvent shows sufficient affinity and capacity for the lower carboxylic acid.

These characteristics are quantifiable from experimentally determined equilibrium partition coefficients as defined in more detail below.

The equilibrium partition coefficient (also used interchangeably with the term "partition coefficient") for component A (the lower carboxylic acid) is defined as follows:

$$P(A) = \frac{\text{weight percent } A \text{ in solvent phase}}{\text{weight percent } A \text{ in aqueous phase}}$$

The partition coefficient is a measure of the relative concentrations of the solute to be extracted in the two phases. The value of the acid partition coefficient is directly related to the amount of solvent that is required to effect a given extraction. Low values of the partition coefficient indicate high levels of solvent are required, and high values of the partition coefficient indicate low levels of solvent are required. Since the acid partition coefficient changes with acid concentration, the minimum amount of solvent required to effect a given amount of acid extraction also changes. Thus, the controlling solvent flow requirement for the extraction is dictated by the lowest value of the acid partition coefficient as the acid concentration varies from the high of the inlet wet acid feed to the low of the outlet acid concentration of the exiting raffinate stream.

The controlling acid partition coefficient may be defined as:

$$P_{cont} = \text{minimum}(P_{raff}, P_{extr})$$

where $P_{raff}$=acid partition coefficient at an acid concentration approaching that desired in the raffinate stream (i.e., at low acid concentration); and $P_{extr}$=acid partition coefficient at an acid concentration approaching that desired in the extract stream (i.e., at high acid concentration).

The most important water-acid selectivity value is that at the extract end of the extraction cascade. It is defined as:

$$R_{extr} = W_{extr}/A_{extr}$$

where $W_{extr}$=weight fraction of water in the extract product stream; and $A_{extr}$=weight fraction of acid in the extract product stream.

The controlling partition coefficient, $P_{cont}$, and extract water-to-acid ratio, $R_{extr}$, may be combined to yield an overall extraction factor, $\epsilon$, which is a simple measure of the efficacy of a given solvent for recovering lower acids from wet acid feeds in an extraction-distillation process. The extraction factor, $\epsilon$, is defined as:

$$\epsilon = P_{cont}/R_{extr} = (P_{cont} * A_{extr})/W_{extr}$$

Generally, the higher the extraction factor, the lower the capital and energy costs are for a given extraction.

Extraction solvents that exhibit the inverse behavior are also known. That is, their acid partition coefficient is lowest at the extract end of the cascade (high acid concentration) and highest at the raffinate end (low acid concentration). Examples of such solvents include nitriles, phosphate esters, phosphine oxides (U.S. Pat. Nos. 3,816,524 and 4,909,939), and amines (e.g., King, "Amine-Based Systems for Carboxylic Acid Recovery: Tertiary Amines and the Proper Choice of Diluent Allow Extraction and Recovery from Water," CHEMTECH, Vol. 5, pp. 285-291 (1992); and Tamada et al., "Extraction of Carboxylic Acids with Amine Extractants. 2. Chemical Interactions and Interpretation of Data," *Ind. Eng. Chem. Res.*, Vol. 29, pp. 1327-1333 (1990)).

This inverse behavior (partition coefficient highest at low acid concentration) has also been observed for a phosphonium- and an ammonium-phosphinate ionic liquid (Blauser et al., "Extraction of butyric acid with a solvent containing ammonium ionic liquid," *Sep. Purif. Technol.*, Vol. 119, pp. 102-111 (2013); Martak et al., "Phosphonium ionic liquids as new, reactive extractants of lactic acid," *Chem. Papers*, Vol. 60, pp. 395-98 (2006)) and a phosphonium carboxylate salt (Oliveira et al., "Extraction of L-Lactic, L-Malic, and Succinic Acids Using Phosphonium-Based Ionic Liquids," *Sep. Purif. Tech.*, Vol. 85, pp. 137-146 (2012)).

In 2004, Martak and Schlosser introduced using phosphonium phosphinate ionic liquids for extracting certain carboxylic acids from aqueous solutions with abstracts at the May 24-28 Meeting of the Slovakian Society of Chemical Engineering (SSCHE) in Tatranské, Slovakia. Jan Martak and Stefan Schlosser, "Screening of ionic liquids for application in solvent extraction and pertraction," 31$^{st}$ *Int'l Conf. of SSCHE*, p. 188 (2004). In this abstract, the authors reported that butyric acid and lactic acid could be extracted by a material referred to as "IL-A", or IL-A in dodecane, much more effectively than in other ionic liquids, such as ethylmethylimidazolium bis(trifluoromethyl)amide (emim-NTf$_2$), octylmethylimidazolium hexafluorphosphate (omim-PF$_6$), and others.

The authors published more complete data for extracting lactic acid with IL-A later that year in the XIX ARS Separatoria (from Zlotky, Poland). Jan Martak and Stefan Schlosser, "Ionic Liquids of Pertraction and Extraction of Organic Acids," 19$^{th}$ *ARS Separatoria*, pp. 106-113 (2004). Two subsequent papers by Martak and Schlosser on the extraction of lactic acid by a phosphonium ionic liquid are consistent with the identity of IL-A being what is known as IL-104 (trihexyl(tetradecyl)phosphonium bis(trimethylpentyl)phosphinate) from Cytec Industries. Jan Martak and Stefan Schlosser, "Phosphonium Ionic Liquids as New, Reactive Extractants of Lactic Acid," *Chem. Papers*, Vol. 60, pp. 395-98 (2006); Jan Martak and Stefan Schlosser, "Extraction of Lactic Acid by Phosphonium Ionic Liquids," *Sep. Purif. Technol.*, Vol. 57, pp. 483-94 (2007). The structure of IL-104 (or P$_{666,14}$-phosphinate) is shown below.

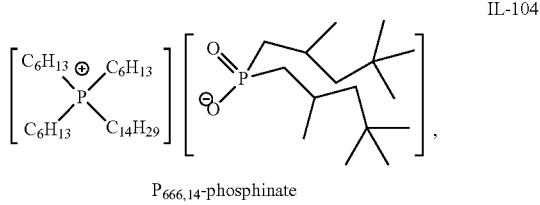

P$_{666,14}$-phosphinate

In the 2006 paper, the authors graphically presented an interesting characteristic of lactic acid extraction by IL-104. It had much stronger partitioning of lactic acid at lower concentrations (see FIG. 11). We describe this as "inverse" because it is more common for covalent organic solvents to have lower partitioning of carboxylic acids at lower aqueous concentrations.

The work of Luis Rebelo and coworkers, however, brought this detail for lactic acid extraction by IL-104 into question. Rebelo et al. reported the performance of three different phosphonium ionic liquids: (1) IL-104; (2) IL-101 (in which a chloride replaced the phosphinate anion); and (3) a third ionic liquid (in which a decanoate anion replaced the phosphinate anion). F. S. Oliveira et al., "Extraction of L-Lactic, L-Malic and Succinic Acids Using Phosphonium-Based Ionic Liquids," *Sep. Purif. Technol.*, Vol. 85, pp. 137-46 (2012). Rebelo et al. showed in FIGS. 2 and 3 that the partitioning of lactic acid between IL-104 and water was diminished at lower (aq) lactic acid concentrations. Thus, some degree of uncertainty was cast on the interesting and opposing observations of Martak and Schlosser. Rebelo et al. did have difficulty with phase behavior and mass accountability of lactic acid, which they attributed to coordination of lactic acid to the phosphinate anion. Formation of a third phase and inverse miscelles also complicated a simple understanding of the studies by Rebelo et al.

In 2008, Martak and Schlosser reported the extraction of butyric acid with IL-104 in dodecane. Jan Martak and Stefan Schlosser, "Liquid-liquid equilibria of butyric acid for solvents containing a phosphonium ionic liquid," *Chem. Papers*, Vol. 62, pp. 42-50 (2008). That system also displayed the inverse behavior described above with higher partitioning at lower concentrations (see FIG. 2). In 2013, the authors substituted an ammonium cation (trioctylmethylammonium) for the phosphonium of IL-104, as shown below. M. Blahusiak et al., "Extraction of butyric acid with a solvent containing ammonium ionic liquid," *Sep. Purif. Technol.*, Vol. 119, pp. 102-11 (2013).

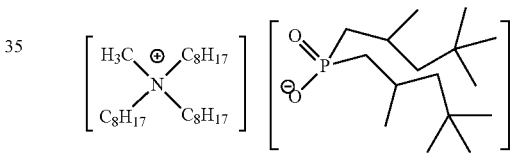

Although the ammonium phosphinate had much greater mutual solubility of water (>20%), much lower thermal stability (decomposing significantly above 150° C. versus 250° C. for the phosphonium phosphinate), and lower solubility in dodecane; it did display the same attractive feature of having a higher extraction efficiency at lower butyric acid concentrations.

Despite the work of Martek et al. and Rebelo et al., there continues to be a need in the art for extraction solvents with excellent partitioning of lower carboxylic acids from aqueous solutions and that enable the simple separation of these acids. There is also a need for extraction solvents with high extraction factors whereby $C_1$ to $C_4$ carboxylic acids can be recovered from wet acid feeds in an energy-efficient and cost-effective manner.

The present invention addresses these needs as well as others, which will become apparent from the following description and the appended claims.

SUMMARY OF THE INVENTION

The invention is set forth in the following detailed description and the appended claims.

Briefly, in one aspect, the present invention provides a solvent for extracting a $C_1$ to $C_4$ carboxylic acid from water. The solvent comprises (a) a quaternary phosphonium phosphinate salt and (b) a co-solvent selected from the group consisting of higher carboxylic acids, ethers, esters, ketones, aromatic hydrocarbons, chlorinated hydrocarbons, and nitriles. The phosphinate salt has the general formula 1:

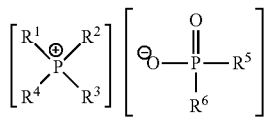

1 wherein $R^1$, $R^2$, $R^3$ and $R^4$ are each independently a $C_1$ to $C_{26}$ hydrocarbyl group, provided that $R^1$, $R^2$, $R^3$, and $R^4$ collectively have a total of at least 24 carbon atoms; and $R^5$ and $R^6$ are each independently an alkyl or aryl group having 3 to 24 carbon atoms and may be connected together with the phosphorus atom to form a heterocyclic ring.

In another aspect, the present invention provides a composition for separating a $C_1$ to $C_4$ carboxylic acid from water. The composition comprises (a) a quaternary phosphonium phosphinate salt according to the invention, (b) a co-solvent according to the invention, (c) a $C_1$ to $C_4$ carboxylic acid, and (d) water.

In yet another aspect, the present invention provides a process for separating a $C_1$ to $C_4$ carboxylic acid from water. The process comprises contacting a feed mixture comprising a $C_1$ to $C_4$ carboxylic acid and water with an extraction solvent according to the invention at conditions effective to form (a) an extract mixture comprising the phosphinate salt, the co-solvent, and at least a portion of the $C_1$ to $C_4$ carboxylic acid from the feed mixture and (b) a raffinate mixture comprising water and less of the $C_1$ to $C_4$ carboxylic acid compared to the feed mixture.

In one embodiment, the present invention is directed to a process for separating acetic acid from water. The process comprises contacting a feed mixture comprising acetic acid and water with an extraction solvent comprising a quaternary phosphonium phosphinate salt according to the invention at conditions effective to form (a) an extract mixture comprising the phosphinate salt and at least a portion of the acetic acid from the feed mixture and (b) a raffinate mixture comprising water and less of the acetic acid compared to the feed mixture.

DETAILED DESCRIPTION OF THE INVENTION

It has been found, surprisingly, that when certain quaternary phosphonium phosphinates and co-solvents are combined with aqueous solutions of a lower carboxylic acid, the resulting partitioning of the lower acid into the phosphonium phosphinate phase can be fairly high, particularly when the concentration of the lower acid is low (e.g., <5 wt %). The phosphinates show superior selectivity for lower acid extraction over co-extraction of water. As a result, the extraction factor, E, is significantly higher for the phosphinates than other classes of lower acid extraction solvents, and are thus particularly useful for recovering lower acids from wet acid streams.

Accordingly, in one aspect, the present invention provides extraction solvents containing quaternary phosphonium phosphinates and co-solvents that are useful for separating lower acids from aqueous streams. The phosphinates are depicted by the general formula 1:

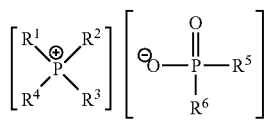

1 wherein $R^1$, $R^2$, $R^3$ and $R^4$ are each independently a $C_1$ to $C_{26}$ hydrocarbyl group, provided that $R^1$, $R^2$, $R^3$, and $R^4$ collectively have a total of at least 24 carbon atoms; and $R^5$ and $R^6$ are each independently an alkyl or aryl group having 3 to 24 carbon atoms and may be connected together with the phosphorus atom to form a heterocyclic ring.

As used herein, the term "hydrocarbyl" refers to a group containing hydrogen and carbon atoms, and may be straight-chained or branched, cyclic or acylic, and saturated or unsaturated.

Each of $R^1$, $R^2$, $R^3$, and $R^4$ may have the same number of carbon atoms or may be of different lengths. In one embodiment, $R^1$, $R^2$, $R^3$, and $R^4$ collectively have not more than 54 carbon atoms. In another embodiment, each of $R^1$, $R^2$, $R^3$, and $R^4$ has at least 6 carbon atoms. In other embodiments, each of $R^1$, $R^2$, $R^3$, and $R^4$ contains from 6 to 24 carbon atoms, 6 to 20 carbon atoms, 6 to 18 carbon atoms, 6 to 14 carbon atoms, or 8 to 14 carbon atoms.

Preferably, $R^5$ and $R^6$ have such lengths that when combined with the quaternary cationic group [$PR^1R^2R^3R^4$], defined as above, the phosphinate anion renders the salt hydrophobic. Each of $R^5$ and $R^6$ may have the same number of carbon atoms or may be of different lengths. In one embodiment, $R^5$ and $R^6$ collectively have not more than 36 carbon atoms. In another embodiment, each of $R^5$ and $R^6$ has at least 4 carbon atoms. In other embodiments, each of $R^5$ and $R^6$ contains from 3 to 20 carbon atoms, 3 to 18 carbon atoms, 3 to 14 carbon atoms, 3 to 12 carbon atoms, 4 to 24 carbon atoms, 4 to 20 carbon atoms, 4 to 18 carbon atoms, 4 to 14 carbon atoms, 4 to 12 carbon atoms, 6 to 24 carbon atoms, 6 to 20 carbon atoms, 6 to 18 carbon atoms, 6 to 14 carbon atoms, 6 to 12 carbon atoms, 8 to 14 carbon atoms, or 8 to 12 carbon atoms.

The alkyl groups represented by $R^5$ and $R^6$ may be branched or straight-chained, and may contain functional groups such as alkoxy, olefinic, and halogen functionalities.

The aryl groups represented by $R^5$ and $R^6$ may be mono- or polycyclic. It may be substituted with a halogen, alkyl group, aryl group, halogen-substituted alkyl group, halogen-substituted aryl group, secondary alkyl or aryl amino group, tertiary alkyl or aryl amino group, halogen-substituted secondary alkyl or aryl amino group, halogen-substituted tertiary alkyl or aryl amino group, nitro group, alkyl or aryl ether group, halogen-substituted alkyl or aryl ether group, or combinations thereof.

$R^5$ and $R^6$ may be connected together with the phosphorus atom to form a heterocyclic ring.

In one embodiment, the phosphinate salt comprises a trihexyl(tetradecyl)-phosphonium cation.

In another embodiment, the phosphinate anion comprises bis(2,4,4-trimethylpentyl)phosphinate.

In a preferred embodiment, the phosphinate salt comprises trihexyl(tetradecyl)phosphonium bis(2,4,4-trimethylpentyl)phosphinate.

By "hydrophobic," it is meant that the salt is immiscible in water at typical extraction conditions, e.g., has less than 5 wt % miscibility in water at 20° C.

The phosphinate salt is the liquid state under typical extraction conditions, e.g., from 20 to 100° C. at atmospheric pressure.

Some of the phosphonium phosphinates having the structure of formula 1 are commercially available from vendors, such as Cytec Industries Inc. The phosphinates may be produced by known methods from readily available precursors. See, e.g., Kogelnig et al., "Greener Synthesis of New Ammonium Ionic Liquids and their Potential as Extracting Agents," *Tetrahedron Letters*, Vol. 49, pp. 2782-2785 (2008) and Ferguson et al., "A Greener, Halide-Free Approach to Ionic Liquid Synthesis," *Pure & Appl. Chem.*, Vol. 84, pp. 723-744 (2012)). The former approach involves the metathesis of an alkali phosphinate with a quaternary ammonium halide, while the latter approach employs an ion-exchange resin. An example of a readily available precursor is trihexyl (tetradecyl)phosphonium chloride.

Mixtures containing more than one quaternary cation and more than one phosphinate anion are also useful for the extraction of lower acids from aqueous solutions and, therefore, are also contemplated as being within the scope of the present invention. Thus, the inventive extraction solvent may comprise two or more of the phosphinate salts.

In addition to the phosphinate salt, the extraction solvent according to the invention comprises a co-solvent. The co-solvent is not the extract (i.e., the $C_1$-$C_4$ carboxylic acid to be separated). Rather, it is separate from and in addition to the lower carboxylic acid to be separated.

The co-solvent is preferably selected to impart desirable physical properties to the extraction solvent, such as lower viscosity or higher hydrophobicity or to provide low-boiling azeotropes with water as described above and illustrated in, for example, U.S. Pat. Nos. 1,861,841; 1,917,391; 2,028,800; 3,052,610; 5,662,780; 2,076,184; and 2,204,616, to enable drying of the lower carboxylic acid in a subsequent purification step.

Examples of such hydrophobic co-solvents include ketones, aromatic hydrocarbons, ethers, esters, chlorinated hydrocarbons, nitriles, and higher carboxylic acids.

Saturated hydrocarbons, such as dodecane, are not preferred as a co-solvent due to azeotropes that can be formed by the saturated hydrocarbon and water. Azeotropes can complicate the purification of the lower carboxylic acid. For instance, dodecane and butyric acid form an azeotrope that would make it very difficult to purify butyric acid from the extract phase of the extractions. Thus, in one embodiment, the extraction solvent according to the invention is free of or substantially free of added saturated hydrocarbons.

Fatty alcohols, such as nonanol, are also not preferred as a co-solvent, since these may complicate the separation of the lower acids by forming esters during extraction or subsequent purification. Thus, in one embodiment, the extraction solvent according to the invention is free of or substantially free of added fatty alcohols.

Preferred co-solvents form minimum-boiling azeotropes with water, but do not form azeotropes with the lower acid.

In one embodiment, the co-solvent has 4 to 20 carbon atoms. In another embodiment, the co-solvent has 4 to 18 carbon atoms. In other embodiments, the co-solvent has 4 to 16 carbon atoms, 4 to 14 carbon atoms, 4 to 12 carbon atoms, 5 to 20 carbon atoms, 5 to 18 carbon atoms, 5 to 16 carbon atoms, 5 to 14 carbon atoms, or 5 to 12 carbon atoms.

In one particular embodiment, the co-solvent comprises a higher carboxylic acid. As used herein, "higher carboxylic acids" refer to a carboxylic acid having 4 to 20 carbon atoms. The higher carboxylic acid may be straight-chained, branched, or aromatic. The "higher carboxylic acid" contains at least 1 more carbon atom than the acid to be separated or has a sufficiently different boiling point (e.g., +/−2° C.) from the lower acid to be separated such that the two may be separated from one another by simple distillation. The higher carboxylic acid may contain additional functional groups, such as alkoxy, olefinic, and halogen.

In one embodiment, the higher carboxylic acid is selected from the group consisting of n-butyric acid, isobutyric acid, n-valeric acid, isovaleric acid, n-hexanoic acid, 2-ethylbutyric acid, heptanoic acid, n-octanoic, 2-ethylhexanoic acids, nonanoic acids, decanoic acids, dodecanoic acids, stearic acid, oleic acid, linolenic acid, and mixed vegetable-derived acids.

In another embodiment, the higher carboxylic acid is selected from the group consisting of n-butyric acid, isobutyric acid, n-valeric acid, isovaleric acid, n-hexanoic acid, 2-ethylbutyric acid, heptanoic acid, n-octanoic acid, and 2-ethylhexanoic acid.

In yet another embodiment, the higher carboxylic acid is selected from the group consisting of benzoic acid, toluic acids, and 3-dimethylaminobenzoic acid.

Preferred co-solvent esters are those containing four to six carbon atoms such as ethyl acetate, n-propyl acetate, n-propyl formate, i-propyl acetate, i-propyl formate, n-butyl acetate, n-butyl formate, i-butyl acetate, i-butyl formate, n-propyl propionate, and i-propyl propionate.

Preferred co-solvent ketones are those containing five to nine carbon atoms such as 2-pentanone, 3-pentanone, 3-methyl-2-butanone, 2-hexanone, 2-heptanone, cyclohexanone, 4-methyl-2-pentanone, 2,4-dimethyl-3-pentanone, 5-methyl-2-hexanone, 4-heptanone, 2-octanone, 5-nonanone, 2,8-dimethyl-4-heptanone, 3,3,5-trimethyl cyclohexanone, and isophorone.

Preferred co-solvent ethers are those containing four to eight carbon atoms such as diethyl ether, methyl propyl ether, dipropyl ether, di-isopropyl ether, methyl tert butyl ether, tertiary amyl methyl ether, and ethyl butyl ether.

Preferred co-solvent aromatic hydrocarbons include toluene, m-xylene, p-xylene, and o-xylene.

Preferred co-solvent chlorinated hydrocarbons include methylene chloride, chloroform, dichloroethane, ethylene chloride, carbon tetrachloride, and chlorinated derivatives of benzene.

Preferred co-solvent nitriles include valeronitrile and nitriles that are higher boiling than valeronitrile, such as hexanenitrile and benzonitrile.

In one embodiment, the hydrophobic co-solvent is selected from the group consisting of methyl isobutyl ketone, toluene, isopropyl acetate, and methyl t-butyl ether.

In another embodiment, the hydrophobic co-solvent is a fatty carboxylic acid, such as butyric, pentanoic, hexanoic, heptanoic, octanoic, nonanoic acids, and isomeric forms of $C_4$-$C_9$ carboxylic acids.

The extraction solvent according to the invention and compositions containing the same may include two or more of the co-solvents. Desirable physical properties of the claimed systems may best be achieved by employing mixtures of the hydrophobic co-solvents.

The extraction solvent of the invention may comprise from 1 to 99 weight percent of the phosphinate salt and from 1 to 99 weight percent of the co-solvent, based on the total weight of the extraction solvent. In certain embodiments, the extraction solvent may contain from 5 to 95, 10 to 95, 15 to 95, 20 to 95, 25 to 95, 30 to 95, 35 to 95, 40 to 95, 45 to 95, 50 to 95, 10 to 90, 20 to 90, 30 to 90, 40 to 90, 50 to 90, 10 to 80, 20 to 80, 30 to 80, 40 to 80, 50 to 80, 10 to 70, 20 to 70, 30 to 70, 40 to 70, 50 to 70, 10 to 60, 20 to 60, 30 to 60, 40 to 60, 50 to 60, 5 to 50, 10 to 50, 15 to 50, 20 to 50, 25 to 50, 30 to 50, 35 to 50, 40 to 50, 5 to 45, 10 to 45, 15 to 45, 20 to 45, 25 to 45, 30 to 45, 35 to 45, 5 to 40, 10 to 40, 15 to 40, 20 to 40, 25 to 40, or 30 to 40 weight percent of the phosphinate salt, and the balance of the extraction solvent may be composed of the co-solvent.

The co-solvent may be combined with the phosphinate salt before introduction into the extraction vessel. Alternatively, the co-solvent may be introduced separately into the extraction vessel. In one embodiment, the co-solvent may be introduced as a second solvent feed on the other side of the extraction cascade from the wet acid feed, such as in a fractional extraction mode, wherein the co-solvent helps to wash any phosphinate from the final raffinate product stream.

The phosphinate or mixture of phosphinates of the present invention may be mixed with one or more of the co-solvents to form the extraction solvent in any known manner.

In a second aspect, the invention provides a composition for separating a $C_1$ to $C_4$ carboxylic acid from water. The composition comprises the phosphinate salt according to formula 1, the co-solvent, a $C_1$ to $C_4$ carboxylic acid, and water. It is useful for separating the lower carboxylic acid from water and optionally purifying the lower acid.

The composition may contain more than one of the phosphinate salt, more than one of the co-solvent, and/or more than one of the lower acid. The phosphinate salt, co-solvent, and lower acid may be any of those described herein.

In one embodiment, the composition has only two liquid phases.

A feature of the composition is that the $C_1$ to $C_4$ carboxylic acid may be recovered by distillation at atmospheric pressure or lower.

The weight ratio of the extraction solvent (phosphinate and co-solvent) to wet acid feed in the composition may vary over a wide range. For example, the ratio may range from 0.2 to 10:1 or, more preferably, from 0.3 to 4:1.

As noted above, the lower acids refer to $C_1$ to $C_4$ carboxylic acids. By way of example, the carboxylic acids may be monocarboxylic acids or organofluorine carboxylic acids. Examples of such acids include formic acid, acetic acid, propionic acid, acrylic acid, n-butyric acid, isobutyric acid, methacrylic acid, trifluoroacetic acid, and the like. In one embodiment, the lower acid comprises acetic acid.

Examples of processes that produce diluted aqueous carboxylic acid-containing streams (i.e., comprising less than 1 weight percent to 60 weight percent of $C_1$ to $C_4$ carboxylic acids in an aqueous mixture, which may be referred to as "wet acid feeds") include the production of cellulose esters or terephthalic acid, the production of ketene or higher ketenes from high temperature dehydration of carboxylic acids and anhydrides, the hydrolysis of poly(vinylacetate), the production of Fischer-Tropsch liquids, oil and gas production (yielding "produced waters"), the ketonization of carboxylic acids to ketones, the oxidation of ethylene to acetaldehyde by the Wacker process, the oxidation of propylene to acrylic acid, the oxidation of oxo aldehydes to their carboxylic acids, hydrocarboxylation of formaldehyde with water and carbon monoxide, the oxidation of isobutylene to methacrylic acid, pyroligneous acids, fermentations broths, vinegar streams, and the like. Vinegar streams refer to aqueous streams containing acetic acid. In one embodiment, the wet acid feed is derived from the production of cellulose esters.

The wet acid feed may comprise from 0.5 to 60 weight percent of one or more of the $C_1$ to $C_4$ carboxylic acids. More preferably, the wet acid feed comprises from 0.5 to 45 weight percent of the $C_1$ to $C_4$ carboxylic acids. Most preferably, the wet acid feed comprises from 0.5 to 35 weight percent of the $C_1$ to $C_4$ carboxylic acids. Because of the unusually high acid partition coefficients of the phosphinate salts of the invention even at low acid concentrations, the extraction solvent of the instant invention may be used advantageously to extract lower acids at concentrations as low as 0.5 weight percent in the wet acid feed.

As used herein, the terms "feed" and "feed mixture" are intended to have their commonly understood meaning in the liquid-liquid extraction art, which is the solution that contains the materials to be extracted or separated. In the present invention, one example of a "feed" is a mixture composed of one or more of formic, acetic, propionic, acrylic, n-butyric, isobutyric, methacrylic, and trifluoroacetic acids in water. In the present invention, the terms "feed" and "feed mixture" are synonymous with "aqueous acid stream," "weak acid stream," and "wet acid feed."

The term "extraction solvent," as used herein, is intended to be synonymous with the term "extractant" and is intended to mean the water-immiscible or hydrophobic liquid that is used in the extraction process to extract materials or solutes from the feed.

A feature of the composition according to the invention is that it separates into two phases, an aqueous and an organic phase, with the lower acid distributed between them. The biphasic nature of the composition is desirable in order to physically separate the lower acid from the aqueous solution. The amount of lower acid distributed between the phases is only limited by the biphasic property of the system. Preferably, the lower acid amount does not exceed a level at which the biphasic nature of the composition is lost. Likewise, other materials may also be present, but only to the extent that the biphasic nature of the system is retained. Complex systems that form more than two phases are not preferred, since such a system can obscure the effective separation of the lower acid.

In a third aspect, the present invention provides a process for separating a $C_1$ to $C_4$ carboxylic acid from water. The process includes the step of contacting a feed mixture comprising a $C_1$ to $C_4$ carboxylic acid and water with an extraction solvent comprising a quaternary phosphonium phosphinate salt according to the invention and a co-solvent according to the invention at conditions effective to form (a) an extract mixture comprising the phosphinate salt, the co-solvent, and at least a portion of the $C_1$ to $C_4$ carboxylic acid from the feed mixture and (b) a raffinate mixture comprising water and less of the $C_1$ to $C_4$ carboxylic acid compared to the feed mixture.

The extraction of the feed mixture (i.e., the contacting step) can be carried out by any means known in the art to intimately contact two immiscible liquid phases and to separate the resulting phases after the extraction procedure. For example, the extraction can be carried out using columns, centrifuges, mixer-settlers, and miscellaneous devices. Some representative examples of extractors include unagitated columns (e.g., spray, baffle tray and packed, perforated plate), agitated columns (e.g., pulsed, rotary agitated, and reciprocating plate), mixer-settlers (e.g., pump-settler, static mixer-settler, and agitated mixer-settler), centrifugal extractors (e.g., those produced by Robatel, Luwesta, deLaval, Dorr Oliver, Bird, CINC, and Podbielniak), and other miscellaneous extractors (e.g., emulsion phase contactor, electrically enhanced extractors, and membrane extractors). A description of these devices can be found in the "Handbook of Solvent Extraction," Krieger Publishing Company, Malabar, Fla., pp. 275-501 (1991). The various types of extractors may be used alone or in any combination.

The extraction may be conducted in one or more stages. The number of extraction stages can be selected based on a number of factors, such as capital costs, achieving high extraction efficiency, ease of operability, the stability of the feed and the extraction solvent, and the extraction conditions. The extraction also can be conducted in a batch or continuous mode of operation. In a continuous mode, the extraction may be carried out in a co-current, a counter-current manner, or as a fractional extraction in which multiple solvents and/or solvent feed points are used to help facilitate the separation. The extraction process also can be conducted in a plurality of separation zones that can be in series or in parallel.

The extraction may be carried out at an extraction solvent: feed mixture weight ratio of, for example, 0.2 to 10:1 or, more preferably, 0.3 to 4:1.

The extraction typically can be carried out at a temperature of 10 to 140° C. For example, the extraction can be conducted at a temperature of 30 to 110° C. The desired temperature range may be constrained further by the boiling point of the extractant components or water. Generally, it is undesirable to operate the extraction under conditions where the extractant boils. In one embodiment, the extractor can be operated to establish a temperature gradient across the extractor in order to improve the mass transfer kinetics or decantation rates.

If the temperature chosen for the extraction is greater than the normal boiling point of any of the lower acid to be extracted, any of the components comprising the extraction solvent, or water; then the extractor may be run under sufficient pressure to suppress boiling of any of aforementioned components. The extraction typically can be carried out at a pressure of 1 bara to 10 bara, or 1 bara to 5 bara.

In one embodiment, the separation process according to the invention may further include the steps of separating the extract from the raffinate and recovering the $C_1$ to $C_4$ carboxylic acid from the extract by distillation at atmospheric pressure or lower. Any known method from separating a liquid extract from a raffinate may be used. Likewise, any known distillation technique may be used to recover the lower acid from the extraction solvent.

In one embodiment, the present invention provides a process for separating acetic acid from water. The process comprises contacting a feed mixture comprising acetic acid and water with an extraction solvent comprising a quaternary phosphonium phosphinate salt according to the invention at conditions effective to form (a) an extract mixture comprising the phosphinate salt and at least a portion of the acetic acid from the feed mixture and (b) a raffinate mixture comprising water and less of the acetic acid compared to the feed mixture.

This acetic acid separation process may be carried out using any of the modes described herein above.

The extraction solvent used in this process may further comprise one or more of the co-solvents according to the invention.

The acetic acid separation process may further include the steps of separating the extract mixture from the raffinate mixture and recovering the acetic acid from the extract mixture by distillation at atmospheric pressure or lower.

These additional steps may also be carried out as described herein above.

The present invention includes and expressly contemplates any and all combinations of embodiments, features, parameters, and/or ranges disclosed herein. That is, the invention may be defined by any combination of embodiments, features, parameters, and/or ranges mentioned herein.

As used herein, the indefinite articles "a" and "an" mean one or more, unless the context clearly suggests otherwise. Similarly, the singular form of nouns includes their plural form, and vice versa, unless the context clearly suggests otherwise.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention.

EXAMPLES

Abbreviations used in the following examples are summarized in Table 1.

TABLE 1

Abbreviations

| Compound | Abbreviation |
|---|---|
| acetic acid | HOAc |
| propionic acid | HOPr |
| n-butyric acid | nHOBu |
| isobutyric acid | iHOBu |

TABLE 1-continued

Abbreviations

| Compound | Abbreviation |
|---|---|
| 4-methyl-2-pentanone | MIBK |
| methyl tert butyl ether | MTBE |
| butyronitrile | PrCN |
| 2-ethylhexanoic acid | 2-EH Acid |
| tertiary amyl methyl ether | TAME |
| 4-heptanone | DPK |
| i-propyl acetate | iPrOAc |
| n-propyl acetate | nPrOAc |
| 5-methyl-2-hexanone | MIAK |
| 2-heptanone | MAK |
| tributyl phosphate | TBP |
| triethylhexyl phosphate | TEHP |
| Cyanex 923: a mixture of trialkyl phosphine oxides with octyl and hexyl groups | C923 |
| 1-ethyl-3-methyl imidazolium bis(trifluoromethylsulfonyl)imide | emim-NTf$_2$ |
| 1-butyl-3-methyl imidazolium bis(trifluoromethylsulfonyl)imide | bmim-NTf$_2$ |
| 1-butyl-3-methyl imidazolium bis(trifluoroethylsulfonyl)imide | bmim-BETI |
| 1-hexyl-3-methyl imidazolium bis(trifluoromethylsulfonyl)imide | hmim-NTf$_2$ |
| 1-octyl-3-methyl imidazolium bis(trifluoromethylsulfonyl)imide | omim-NTf$_2$ |
| 1-octyl-3-methyl imidazolium bis(trifluoroethylsulfonyl)imide | omim-BETI |
| 1-decyl-3-methyl imidazolium bis(trifluoromethylsulfonyl)imide | C$_{10}$mim-NTf$_2$ |
| 1-butyl-2,3-dimethyl imidazolium bis(trifluoromethylsulfonyl)imide | C$_4$mmim-NTf$_2$ |
| 1-(8-hydroxyoctyl)-3-methylimidazolium bis(trifluoromethylsulfonyl)imide | HOC$_8$mim-NTf$_2$ |
| dimethylaminoethyl-dimethylethylammonium bis(trifluoromethyl)sulfonylimide | iPr$_2$N(CH$_2$)$_2$mim-NTf$_2$ |
| 1-butyl pyridinium bis(trifluoromethylsulfonyl)imide | bpyr-NTf$_2$ |
| 1-(2-methoxyethyl)-pyridinium tris(pentafluoroethyl)trifluorophosphate | MeOEtpyr-FAP |
| 1-(4-cyanobutyl)-3-methyl imidazolium bis(trifluoromethylsulfonyl)imide | (4-CN)bmim-NTf$_2$ |
| trimethyl(butyl)ammonium bis(trifluoromethylsulfonyl)imide | N$_{1114}$-NTf$_2$ |
| trimethyl(octyl)ammonium bis(trifluoromethylsulfonyl)imide | N$_{1118}$-NTf$_2$ |
| 1-(2-diisopropylaminoethyl) dimethylethylammonium bis(trifluoromethyl)sulfonylimide | iPr$_2$N(CH$_2$)$_2$N$_{211}$-NTf$_2$ |
| dimethylaminoethyl-dimethylethylammonium bis(trifluoromethyl)sulfonylimide | Me$_2$N(CH$_2$)$_2$N$_{211}$-NTf$_2$ |
| choline bis(trifluoromethylsulfonyl)imide | choline-NTf$_2$ |
| 1-butyl-1-methyl pyrrolidinium bis(trifluoromethylsulfonyl)imide | C4mpyrr-NTf$_2$ |
| triethyl(octyl)phosphonium bis(trifluoromethylsulfonyl)imide | P$_{2228}$-NTf$_2$ |
| trioctyl(methyl)phosphonium bis(trifluoromethylsulfonyl)imide | P$_{8881}$-NTf$_2$ |
| 1-(2-diisopropylaminoethyl) trioctylphosphonium bis(trifluoromethyl)sulfonylimide | iPr$_2$N(CH$_2$)$_2$P$_{888}$-NTf$_2$ |
| trihexyl(tetradecyl)phosphonium chloride | P$_{666,14}$-Cl |
| trihexyl(tetradecyl)phosphonium hydroxide | P$_{666,14}$-OH |
| trihexyl(tetradecyl)phosphonium bis(trifluoromethylsulfonyl)imide | P$_{666,14}$-NTf$_2$ |
| trihexyl(tetradecyl)phosphonium tris(pentafluoroethyl)trifluorophosphate | P$_{666,14}$-FAP |
| trihexyl(tetradecyl)phosphonium bis(2,4,4-trimethylpentyl)phosphinate | P$_{666,14}$-phosphinate |

Example 1

Extraction of Acetic Acid Using Non-Ionic Solvents

Tie line data at both high (typically around 16-20 wt % of HOAc in the organic phase) and low acetic acid concentrations (typically around 1 to 5 wt % of HOAc in the organic phase) were measured for each solvent at the temperature given in Table 2.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent.

These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$, and extraction factor, $\epsilon$. Results are given in Table 2.

TABLE 2

Acetic Acid Extraction Factors of Non-Ionic Solvents

| Co-Solvent | T (° C.) | $P_{cont}$ | HOAc at $P_{cont}$ (wt %) | $R_{extr}$ | Extraction Factor ($\epsilon$) |
|---|---|---|---|---|---|
| ethyl acetate | 25 | 0.99 | 1.5 | 0.98 | 1.01 |
| n-butyl acetate | 40 | 0.41 | 1.6 | 0.52 | 0.79 |
| MIBK | 35 | 0.65 | 1.6 | 0.53 | 1.23 |
| MTBE | 40 | 0.7 | 2.0 | 0.5 | 1.40 |
| PrCN | 20 | 2.85 | 17.0 | 0.7 | 4.07 |
| 2-EH Acid | 40 | 0.32 | 1.3 | 0.29 | 1.10 |
| TAME | 40 | 0.42 | 1.5 | 0.34 | 1.24 |
| DPK | 40 | 0.32 | 1.3 | 0.31 | 1.03 |
| iPrOAc | 40 | 0.54 | 1.8 | 0.65 | 0.83 |
| isophorone | 40 | 1.1 | 1.2 | 0.67 | 1.64 |
| nPrOAc | 40 | 0.51 | 2.2 | 0.70 | 0.73 |
| MIAK | 40 | 0.46 | 1.7 | 0.34 | 1.35 |
| MAK | 40 | 0.49 | 1.7 | 0.41 | 1.20 |
| 2-hexanone[a] | 35 | 0.91 | 3.9 | 0.97 | 0.93 |

[a]Data taken from J. Chem. Eng. Data, Vol. 46, pp. 1450-56 (2001).

Although PrCN has a relatively high extraction factor, it has the same boiling point as acetic acid, forms an azeotrope with acetic acid, and is thus very difficult to separate from acetic acid.

Example 2

Extraction of Acetic Acid Using Phosphate Ester Solvents

Tie line data at both high (typically around 15-20 wt % of HOAc in the organic phase) and low acetic acid concentrations (typically around 1 to 2 wt % of HOAc in the organic phase) were measured for each solvent (either a pure phosphate ester or a mixture of phosphate ester with a co-solvent) at the temperature given in Table 3.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent.

These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$, and extraction factor, $\epsilon$. Results are given in Table 3.

TABLE 3

Acetic Acid Extraction Factors for Solvents Containing Phosphate Esters at 40° C.

| Solvent | $P_{cont}$ | HOAc at $P_{cont}$ (wt %) | $R_{extr}$ | Extraction Factor ($\epsilon$) |
|---|---|---|---|---|
| tributyl phosphate (TBP) | 0.78 | 18.1 | 0.39 | 2.00 |
| 25 wt % TBP, 75 wt % MTBE | 0.94 | 19.7 | 0.52 | 1.81 |
| 25 wt % TBP, 75 wt % iPrOAc | 0.80 | 18.1 | 0.61 | 1.31 |
| triethylhexyl phosphate (TEHP) | 0.33 | 16.2 | 0.12 | 2.75 |
| 25 wt % TEHP, 75 wt % MTBE | 0.71 | 16.9 | 0.30 | 2.37 |
| 25 wt % TEHP, 75 wt % iPrOAc | 0.62 | 15.8 | 0.39 | 1.59 |

As expected from Wardell and King ("Solvent Equilibria for Extraction of Carboxylic Acids from Water," *J. Chem. and Eng. Data*, Vol. 23, No. 2, pp. 144-148 (1978)), the extraction factors of the phosphate esters alone were somewhat better than those of the phosphate esters with co-solvents.

Example 3

Extraction of Acetic Acid Using Cyanex 923

Cyanex 923 is a commercially available mixture of trihexyl and dioctyl phosphine oxides.

Tie line data at both high (typically around 15-20 wt % of HOAc in the organic phase) and low acetic acid concentrations (typically around 1 to 2 wt % of HOAc in the organic phase) were measured for each solvent (either commercially available Cyanex 923 or a mixture of Cyanex 923 with a co-solvent) at the temperature given in Table 4.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent.

These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$, and extraction factor, $\epsilon$. Results are given in Table 4.

TABLE 4

Acetic Acid Extraction Factors for Solvents Containing Cyanex at 40° C.

| Solvent | $P_{cont}$ | HOAc at $P_{cont}$ (wt %) | $R_{extr}$ | Extraction Factor ($\epsilon$) |
|---|---|---|---|---|
| Cyanex 923 (C923) | 0.94 | 19.0 | 0.26 | 3.62 |
| 75 wt % MTBE/25 wt % C923 | 0.89 | 20.0 | 0.36 | 2.47 |
| 75 wt % iPrOAc/25 wt % C923 | 0.77 | 20.0 | 0.43 | 1.79 |

Example 4

Extraction of Acetic Acid Using $P_{666,14}$-Phosphinate

Tie line data at both high (typically around 15-20 wt % of HOAc in the organic phase) and low acetic acid concentrations (typically around 1 to 2 wt % of HOAc in the organic phase) were measured for each solvent (either $P_{666,14}$-phosphinate alone, or a mixture of $P_{666,14}$-phosphinate with a co-solvent) at 40° C.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent.

These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$, and extraction factor, $\epsilon$. Results are given in Table 5.

TABLE 5

Extraction of Acetic Acid with Solvents Containing $P_{666,14}$-phosphinate

| Solvent | $P_{cont}$ | HOAc at $P_{cont}$ (wt %) | $R_{extr}$ | Extraction Factor ($\epsilon$) |
|---|---|---|---|---|
| $P_{666,14}$-phosphinate | 1.49 | 17.3 | 0.20 | 7.45 |
| 75 wt % MTBE/25 wt % $P_{666,14}$-phosphinate | 0.98 | 18.5 | 0.26 | 3.77 |
| 65 wt % iPrOAc/35 wt % $P_{666,14}$-phosphinate | 0.88 | 18.0 | 0.45 | 1.95 |

Example 5

Extraction of Acetic Acid Using Various Hydrophobic Liquid Salts

Tie line data at both high (typically around 7-25 wt % of HOAc in the organic phase) and low acetic acid concentrations (typically around 0.2 to 5 wt % of HOAc in the organic phase) were measured for each solvent at the temperature specified in Table 6.

Some solvents showed extremely low acid partition coefficients, and the two-phase region did not extend much above about 7 wt % of acetic acid. Equilibrium data were measured for each compound in the following manner.

Three grams of the solvent were pipetted into a jacketed glass cell, wherein three grams of an aqueous mixture of acetic acid (prepared to yield either high or low acid concentration data) were added. A stir bar was introduced to the vial and the contents sealed with a plastic cap and a layer of parafilm tape. The cell was maintained at the desired temperature by means of a thermostatted fluid circulating through the cell jacket. The mixture was agitated vigorously for 1.5 hours and then allowed to separate into clear phases while maintaining the specified temperature without stirring. After a six hour settling time, each phase was sampled and analyzed by NMR for water and acetic acid weight percent.

These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$, and extraction factor, $\epsilon$. Results are given in Table 6.

TABLE 6

Extraction of Acetic Acid in a Selection of Hydrophobic Solvents at 20° C.

| Solvent | $P_{cont}$ | HOAc at $P_{cont}$ (wt %) | $R_{extr}$ | Extraction Factor ($\epsilon$) |
|---|---|---|---|---|
| emim-NTf$_2$ | 0.30 | 7.1 | 0.85 | 0.35 |
| bmim-NTf$_2$ | 0.21 | 1.4 | 0.69 | 0.31 |
| bmim-NTf$_2^b$ | 0.24 | 5.4 | 0.79 | 0.30 |
| bmim-FAP$^b$ | 0.06 | 1.7 | 0.33 | 0.18 |
| bmim-BETI | 0.06 | 0.6 | 0.39 | 0.15 |
| hmim-NTf$_2$ | 0.19 | 4.6 | 0.56 | 0.34 |
| omim-NTf$_2$ | 0.18 | 0.9 | 0.47 | 0.38 |
| omim-NTf$_2^a$ | 0.12 | 11.8 | 0.68 | 0.17 |
| omim-BETI | 0.05 | 0.5 | 0.50 | 0.11 |
| C$_{10}$mim-NTf$_2$ | 0.13 | 3.6 | 0.39 | 0.34 |
| C$_4$mmim-NTf$_2$ | 0.13 | 1.1 | 0.59 | 0.22 |
| iPr$_2$N(CH$_2$)$_2$mim-NTf$_2$ | 0.18 | 4.5 | 0.88 | 0.20 |
| MeOEtmim-FAP | 0.04 | 0.3 | 0.23 | 0.15 |
| 4CNbmim-NTf$_2$ | 0.65 | 11.0 | 0.82 | 0.79 |
| HOC$_8$mim-NTf$_2$ | 0.54 | 7.6 | 0.98 | 0.55 |
| (C$_6$F$_{13}$)—(C$_2$H$_4$)mim-NTf$_2$ | 0.08 | 0.7 | 0.60 | 0.13 |

TABLE 6-continued

Extraction of Acetic Acid in a Selection of Hydrophobic Solvents at 20° C.

| Solvent | $P_{cont}$ | HOAc at $P_{cont}$ (wt %) | $R_{extr}$ | Extraction Factor ($\epsilon$) |
|---|---|---|---|---|
| C$_4$mpyrr-NTf$_2$ | 0.33 | 9.5 | 0.45 | 0.74 |
| bpyr-NTf$_2$ | 0.22 | 5.1 | 0.69 | 0.31 |
| MeOEtpyr-FAP | 0.06 | 0.2 | 0.23 | 0.26 |
| N$_{1114}$-NTf$_2$ | 0.13 | 1.9 | 0.84 | 0.16 |
| N$_{1118}$-NTf$_2$ | 0.06 | 1.2 | 0.47 | 0.14 |
| Me$_2$N(CH$_2$)$_2$N$_{211}$-NTf$_2$ | 0.53 | 9.5 | 2.00 | 0.26 |
| iPr$_2$N(CH$_2$)$_2$N$_{211}$-NTf$_2$ | 0.14 | 4.0 | 0.77 | 0.19 |
| N$_{8881}$-phosphinate | 1.56 | 19.2 | 0.35 | 4.46 |
| choline-NTf$_2$ | 0.82 | 14.0 | 1.64 | 0.50 |
| P$_{2228}$-NTf$_2$ | 0.10 | 2.8 | 0.33 | 0.30 |
| P$_{8881}$-NTf$_2$ | 0.05 | 0.8 | 0.43 | 0.13 |
| iPr$_2$N(CH$_2$)$_2$P$_{888}$-NTf$_2$ | 0.21 | 5.4 | 0.74 | 0.28 |
| P$_{666,14}$-Cl | 0.38 | 8.5 | 0.63 | 0.60 |
| P$_{666,14}$-NTf2 | 0.06 | 1.8 | 0.88 | 0.07 |
| P$_{666,14}$-FAP | 0.02 | 0.1 | 0.23 | 0.10 |

$^a$Equilibration at 75° C. rather than 20° C.
$^b$Data taken from Hashikawa, JP Appl. Kokai 2014/40389.

Example 6

Extraction of Acetic Acid Using P$_{666,14}$-Phosphinate with iPrOAc as Co-Solvent Tie line data were measured at 40° C. for several solvent mixtures varying from 100 wt % P$_{666,14}$-phosphinate/0 wt % iPrOAc to 0 wt % P$_{666,14}$-phosphinate/100 wt % iPrOAc.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent.

These data were used to calculate partition coefficients, with the controlling partition coefficient, $P_{cont}$, taken as the lesser of the partition coefficients at high and low acid concentrations. The data were also used to calculate the water to acetic acid weight ratio at high acid concentration, $R_{extr}$, extraction factor, $\epsilon$, and the partition coefficient, $P_{HOAc}$, at low acid concentration. Results are given in Table 7.

TABLE 7

Acetic Acid Extraction with P$_{666,14}$-phosphinate and/or iPrOAc

| Extraction Solvent | | | | | | | |
|---|---|---|---|---|---|---|---|
| P$_{666,14}$-phosphinate (wt %) | iPrOAc (wt %) | $P_{cont}$ | HOAc at $P_{cont}$ (wt %) | $R_{extr}$ | Extraction Factor ($\epsilon$) | HOAc at Low Conc. $P_{HOAc}$ (wt %) | Low Conc. $P_{HOAc}$ |
| 100 | 0 | 1.49 | 17.3 | 0.20 | 7.45 | 1.1 | 6.2 |
| 90 | 10 | 0.92 | 18.5 | 0.28 | 3.32 | 1.5 | 4.2 |
| 35 | 65 | 0.88 | 18.0 | 0.45 | 1.95 | 1.8 | 6.9 |
| 10 | 90 | 0.84 | 18.9 | 0.55 | 1.52 | 1.3 | 1.7 |
| 0 | 100 | 0.54 | 1.80 | 0.65 | 0.83 | 1.80 | 0.5 |

As seen from the data in Table 7, adding a small amount of $P_{666,14}$-phosphinate to a conventional organic solvent significantly enhanced the lower acid extraction at low concentration. Thus, lower acids at low concentrations can be extracted more economically using mixtures of $P_{666,14}$-phosphinate and an ester co-solvent than using the ester alone.

Example 7

Extraction of Acetic Acid Using Salts Containing $P_{666,14}$ Cation and Various Anions In each case, the salt was mixed with MIBK in a 1:1 weight ratio, and tie line data were measured at 20° C. for an acetic acid concentration of about 10-15 wt % of HOAc in the organic phase.

In each experiment, roughly equal masses of water and solvent mixture (1:1 weight ratio of liquid salt and MIBK) were added to a glass vial. Acetic acid was added to the solvent-water mixture. Once the acetic acid was added, the mixture was agitated vigorously, and subsequently was allowed to separate into clear phases while maintaining the specified temperature. Each phase was sampled and analyzed by NMR for water and acetic acid weight percent.

These data were used to calculate partition coefficients of acetic acid at the given acid concentration, $P_{HOAc}$. The tie line data were also used to calculate the water to acetic acid weight ratio, $R_{extr}$, and extraction factor, $\epsilon$, at the given acid concentrations. Results are given in Table 8, with a comparison of pure MIBK to the liquid salt/MIBK mixtures.

TABLE 8

Influence of Anion on Extraction of Acetic Acid with $P_{666,14}$ Salts at 20° C.

| Solvent | $P_{HOAc}$ | HOAc at $P_{HOAc}$ (wt %) | $R_{extr}$ | Extraction Factor ($\epsilon$) |
|---|---|---|---|---|
| pure MIBK | 0.81 | 13.0 | 0.74 | 1.10 |
| $P_{666,14}$-Cl + MIBK | 1.00 | 13.9 | 0.75 | 1.34 |
| $P_{666,14}$-NTf2 + MIBK | 0.44 | 5.6 | 0.60 | 0.74 |
| $P_{666,14}$-FAP + MIBK | 0.22 | 5.1 | 0.56 | 0.40 |
| $PP_{666,14}$-BF4 + MIBK | 0.61 | 10.8 | 0.64 | 0.96 |
| $P_{666,14}$-phosphinate + MIBK | 1.11 | 15.0 | 0.50 | 2.23 |

As seen from Table 8, the solvent mixtures containing $P_{666,14}$-NTf$_2$ and $P_{666,14}$-FAP showed low acid partition coefficient, resulting in relatively low acid concentrations.

Example 8

Extraction of Acetic Acid Using $P_{666,14}$-Phosphinate with MIBK as Co-Solvent Tie line data were measured at the specified temperature for several solvent mixtures varying from 100 wt % $P_{666,14}$-phosphinate/0 wt % MIBK to 0 wt % $P_{666,14}$-phosphinate/100 wt % MIBK.

Roughly equal masses of water and solvent were added to a glass vial. Acetic acid was added to the solvent-water mixture in amounts sufficient to give a concentration of about 10-15 wt % of acetic acid in the organic phase. Once the acetic acid was added, the mixture was agitated vigorously, and subsequently was allowed to separate into clear phases while maintaining the specified temperature. Each phase was sampled and analyzed by NMR for water and acetic acid weight percent.

These data were used to calculate partition coefficients of acetic acid at the given acid concentration, $P_{HOAc}$. The tie line data were also used to calculate the water to acetic acid weight ratio, $R_{extr}$, and extraction factor, $\epsilon$, at the given acid concentration. Results are given in Table 9, with a comparison of pure MIBK and pure $P_{666,14}$-phosphinate to the $P_{666,14}$-phosphinate/MIBK mixtures.

TABLE 9

Acetic Acid Extraction with $P_{666,14}$-phosphinate and/or MIBK

| Solvent | MIBK to $P_{666,14}$-phosphinate Weight Ratio | Temp (° C.) | $P_{HOAc}$ | HOAc at $P_{HOAc}$ (wt %) | $R_{extr}$ | Extraction Factor ($\epsilon$) |
|---|---|---|---|---|---|---|
| pure MIBK | 1:0 | 20 | 0.81 | 13.0 | 0.74 | 1.10 |
| MIBK + $P_{666,14}$-phosphinate | 4:1 | 20 | 0.89 | 13.0 | 0.66 | 1.35 |
| MIBK + $P_{666,14}$-phosphinate | 1:1 | 20 | 1.14 | 15.0 | 0.50 | 2.27 |
| MIBK + $P_{666,14}$-phosphinate | 1:8 | 20 | 1.74 | 16.8 | 0.42 | 4.17 |
| MIBK + $P_{666,14}$-phosphinate | 1:24 | 20 | 1.84 | 16.7 | 0.36 | 5.15 |
| $P_{666,14}$-phosphinate | 0:1 | 40 | 1.49 | 17.3 | 0.2 | 7.45 |

As seen from Table 9, adding a small amount of $P_{666,14}$-phosphinate to a conventional organic solvent significantly enhanced lower acid extraction at low concentration. Thus, lower acids at low concentrations can be extracted more economically using mixtures of $P_{666,14}$-phosphinate and a ketone co-solvent than using the ketone alone.

Example 9

Temperature Effect on Extraction of Acetic Acid with Mixture of $P_{666,14}$-Phosphinate and iPrOAc A solvent mixture comprising 90:10 weight ratio of $P_{666,14}$-phosphinate:iPrOAc was used.

Tie line data were measured at 22, 40, 60, and 75° C.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent.

These data were used to calculate partition coefficients, with the controlling partition coefficient, $P_{cont}$, taken as the lesser of the partition coefficients at high and low acid concentrations. The tie line data were also used to calculate the water to acetic acid weight ratio, $R_{extr}$, and extraction factor, $\epsilon$, at the given acid concentration. Results are given in Table 10.

TABLE 10

Effect of Temperature on the Extraction of Acetic Acid

| T (° C.) | $P_{cont}$ | HOAc at $P_{cont}$ (wt %) | $R_{extr}$ | Extraction Factor ($\epsilon$) |
|---|---|---|---|---|
| 22 | 0.66 | 26.6 | 0.25 | 2.60 |
| 40 | 0.65 | 26.4 | 0.23 | 2.79 |
| 60 | 0.66 | 25.9 | 0.26 | 2.55 |
| 75 | 0.59 | 24.1 | 0.25 | 2.36 |

Example 10

Extraction of Acetic Acid Using $P_{666,14}$-Phosphinate and p-Xylene

Tie line data were measured at the specified temperature for several solvent mixtures varying from 100 wt % $P_{666,14}$-phosphinate/0 wt % p-xylene to 0 wt % $P_{666,14}$-phosphinate/100 wt % p-xylene.

Roughly equal masses of water and solvent were added to a glass vial. Acetic acid was added to the solvent-water mixture in amounts sufficient to give a concentration of about 8-18 wt % acetic acid in the organic phase. Once the acetic acid was added, the mixture was agitated vigorously, and subsequently was allowed to separate into clear phases while maintaining the specified temperature. Each phase was sampled and analyzed by NMR for water and acetic acid weight percent.

These data were used to calculate partition coefficients of acetic acid at the given acid concentration, $P_{HOAc}$. The tie line data were also used to calculate the water to acetic acid weight ratio, $R_{extr}$, and extraction factor, $\epsilon$, at the given acid concentration. Results are given in Table 11, with a comparison of pure p-xylene and pure $P_{666,14}$-phosphinate to the $P_{666,14}$-phosphinate/p-xylene mixtures.

TABLE 11

Acetic Acid Extraction with $P_{666,14}$-phosphinate and/or p-Xylene

| Solvent | p-Xylene to $P_{666,14}$-phosphinate Weight Ratio | Temp. (° C.) | $P_{HOAc}$ | HOAc at $P_{HOAc}$ (wt %) | $R_{extr}$ | Extraction Factor ($\epsilon$) |
|---|---|---|---|---|---|---|
| pure p-xylene | 1:0 | 20 | 0.06 | 1.7 | 0.00 | N/A |
| p-xylene + $P_{666,14}$-phosphinate | 4:1 | 20 | 0.37 | 8.1 | 0.23 | 1.65 |
| p-xylene + $P_{666,14}$-phosphinate | 1:1 | 20 | 0.86 | 13.5 | 0.28 | 3.07 |
| p-xylene + $P_{666,14}$-phosphinate | 1:8 | 20 | 1.78 | 17.4 | 0.34 | 5.22 |
| p-xylene + $P_{666,14}$-phosphinate | 1:24 | 20 | 1.95 | 18.0 | 0.37 | 5.34 |
| $P_{666,14}$-phosphinate | 0:1 | 40 | 1.49 | 17.3 | 0.2 | 7.45 |

As seen from Table 11, adding $P_{666,14}$-phosphinate to a poor conventional organic solvent significantly enhanced the partition coefficient for acetic acid. Thus, lower acids can be extracted economically with a mixture of $P_{666,14}$-phosphinate and a normally poor non-ionic organic solvent.

Example 11

Effect of Temperature on Viscosity and Density of $P_{666,14}$-Phosphinate

The viscosity and density of $P_{666,14}$-phosphinate were measured at 20 and 70° C. Results are shown in Table 12.

TABLE 12

Effect of Temperature on Viscosity and Density of $P_{666,14}$-phosphinate

| | 20° C. | 70° C. |
|---|---|---|
| Density of $P_{666,14}$-phosphinate (g/cc) | 0.894 | 0.864 |
| Viscosity of $P_{666,14}$-phosphinate (cP) | 1224 | 113 |

As seen from Table 12, both viscosity and density are inversely related to temperature. Higher temperature operation would enhance the density difference between the extract and raffinate phases. The viscosity of $P_{666,14}$-phosphinate decreased considerably with increasing temperature, which can enhance mass transfer and thus extraction efficiency.

Procedures for Examples 12-19

Continuous Extraction of Acetic Acid Using Mixture of $P_{666,14}$-Phosphinate and iPrOAc In Examples 12 to 19, the extraction of acetic acid from aqueous solutions was performed in a continuous, multi-stage, counter-current, Karr Column with an internal diameter of $^{11}\!/_{16}$ inches. The column was made out of glass, with a glass jacket connected to a recirculating bath for temperature control. The top and bottom settling zones were approximately 80 mL each, while the agitated section was close to 520 mL. The agitation, usually set at 70-90% from flooding, was controlled by adjusting the strokes per minute (SPM) and could be adjusted between 30 to 300 SPM. The weak acid and solvent feeds were charged to the respective vessels and kept at temperature under a nitrogen blanket. The flow rate of the feeds and bottom product were controlled with piston pumps that could be adjusted to deliver between 1 to 500 mL/min. The bottom-phase product was collected in a vessel at temperature. The top-phase product overflowed into a collection vessel at temperature. In this case, the organic phase, being lighter than the aqueous phase, was fed to the bottom of the reciprocating plates while the weak acid aqueous phase was fed to the top. The phases were contacted in a counter-current manner and were allowed to disengage in the top and bottom settling zones.

The composition of the solvents and weak acid feeds are shown in Tables 13 and 14, respectively. A summary of the counter-current extractions using a Karr Column is shown in Table 15. Results are shown in Tables 16-23.

TABLE 13

Extraction Solvent Compositions

| | Extraction Solvent Composition (wt %) | | | |
|---|---|---|---|---|
| Solvent No. | $P_{666,14}$-phosphinate | Isopropyl Acetate | Acetic Acid | Butyric Acid |
| 1 | 0.0 | 100.0 | 0.0 | 0.0 |
| 2 | 44.0 | 54.2 | 1.8 | 0.0 |
| 3 | 38.3 | 59.9 | 1.8 | 0.0 |
| 4 | 38.3 | 59.9 | 0.0 | 1.8 |

TABLE 14

Feed Compositions

| | Feed Composition (wt %) | |
|---|---|---|
| Feed | Water | Acetic Acid |
| A | 66.0 | 34.0 |
| B | 96.6 | 3.4 |

TABLE 15

Extraction Conditions

| Example No. | Solvent No. | Feed | Temp. (° C.) | SPM | Solvent/Feed Ratio (v/v) |
|---|---|---|---|---|---|
| 12 | 1 | A | 40 | 175 | 1.3 |
| 13 | 1 | A | 40 | 175 | 0.9 |
| 14 | 3 | A | 40 | 55 | 0.9 |
| 15 | 3 | A | 40 | 55 | 1.7 |
| 16 | 2 | A | 40 | 95 | 1.9 |
| 17 | 2 | A | 40 | 95 | 0.9 |
| 18 | 2 | B | 40 | 95 | 1.9 |
| 19 | 4 | B | 40 | 95 | 1.9 |

Example 12

Following the above procedures, the complete recovery of acetic acid from a weak acid feed using pure isopropyl acetate as the solvent was performed. The extraction was carried out at a solvent to feed ratio of 1.3 and an agitation of 175 SPM. Other conditions and the results are shown in Table 16.

TABLE 16

Complete Acetic Acid Recovery with Pure Isopropyl Acetate

| | Feed | Solvent | Raffinate | Extract | Component Mass Balance | Mass Balance |
|---|---|---|---|---|---|---|
| Flow Rate (g/min) | 10.28 | 13.05 | 5.13 | 18.30 | — | 100.4 |
| | | | | | | Acetic Acid Recovery (wt %) |
| Acetic Acid (wt %) | 33.91 | 0.13 | 0.15 | 18.54 | 97.1 | 97.3 |
| Water (wt %) | 64.92 | 4.06 | 97.56 | 12.00 | 100.0 | Ratio of Water/Acetic Acid in Extract (lb/lb) |
| Isopropyl Acetate (wt %) | 1.17 | 95.81 | 2.30 | 69.46 | 101.6 | 0.65 |
| $P_{666,14}$-phosphinate (wt %) | — | — | — | — | — | |

Example 13

Following the above procedures, the partial recovery of acetic acid from a weak acid feed using pure isopropyl acetate as the solvent was performed. The extraction was carried out at a solvent to feed ratio of 0.91 and an agitation of 175 SPM. Other conditions and the results are shown in Table 17.

TABLE 17

Partial Recovery of Acetic Acid with Pure Isopropyl Acetate

| | Feed | Solvent | Raffinate | Extract | Component Mass Balance | Mass Balance |
|---|---|---|---|---|---|---|
| Flow Rate (g/min) | 12.00 | 10.88 | 5.58 | 16.47 | — | 96.4 |
| | | | | | | Acetic Acid Recovery (%) |
| Acetic Acid (wt %) | 33.91 | 0.13 | 0.52 | 23.58 | 95.82 | 95.4 |
| Water (wt %) | 64.92 | 4.06 | 97.59 | 14.46 | 106.25 | Ratio of Water/Acetic Acid (lb/lb) |
| Isopropyl Acetate (wt %) | 1.17 | 95.81 | 1.89 | 61.96 | 90.57 | 0.61 |
| $P_{666,14}$-phosphinate (wt %) | — | — | — | — | — | |

Example 14

Following the above procedures, the partial recovery of acetic acid from a weak acid feed using a solvent mixture containing $P_{666,14}$-phosphinate, isopropyl acetate, and a residual amount of acetic acid was performed. The extraction was carried out at a solvent to feed ratio of 0.91 and an agitation of 55 SPM. Other conditions and the results are shown in Table 18.

TABLE 18

Partial Recovery of Acetic Acid with Solvent Mixture Containing $P_{666,14}$-phosphinate, Isopropyl Acetate, and Acetic Acid

| | Feed | Solvent | Raffinate | Extract | Component Mass Balance | Mass Balance |
|---|---|---|---|---|---|---|
| Flow Rate (g/min) | 13.09 | 11.89 | 7.10 | 18.05 | — | 100.7 |
| | | | | | | Acetic Acid Recovery (%) |
| Acetic Acid (wt %) | 33.67 | 1.63 | 3.13 | 23.47 | 96.88 | 96.1 |
| Water (wt %) | 64.55 | 1.99 | 94.61 | 11.12 | 100.47 | Ratio of Water/Acetic Acid (lb/lb) |
| Isopropyl Acetate (wt %) | 1.78 | 58.06 | 2.20 | 40.32 | 104.16 | 0.47 |
| $P_{666,14}$-phosphinate (wt %) | 0.00 | 38.20 | 0.06 | 25.09 | 99.47 | |

Example 15

Following the above procedures, the partial recovery of acetic acid from a weak acid feed using a solvent mixture containing $P_{666,14}$-phosphinate, isopropyl acetate, and a residual amount of acetic acid was performed. The extraction was carried out at a solvent to feed ratio of 1.7 and an agitation of 55 SPM. Other conditions and the results are shown in Table 19.

TABLE 19

Partial Recovery of Acetic Acid with Solvent Mixture Containing $P_{666,14}$-phosphinate, Isopropyl Acetate, and Acetic Acid

| | Feed | Solvent | Raffinate | Extract | Component Mass Balance | Mass Balance |
|---|---|---|---|---|---|---|
| Flow Rate (g/min) | 9.22 | 15.74 | 4.81 | 20.38 | — | 100.9 |
| | | | | | | Acetic Acid Recovery (%) |
| Acetic Acid (wt %) | 33.67 | 1.63 | 1.08 | 16.60 | 102.23 | 109.0 |
| Water (wt %) | 64.55 | 1.99 | 96.58 | 7.62 | 98.98 | Ratio of Water/Acetic Acid (lb/lb) |
| Isopropyl Acetate (wt %) | 1.78 | 58.06 | 2.27 | 48.32 | 107.02 | 0.46 |
| $P_{666,14}$-phosphinate (wt %) | 0.00 | 38.32 | 0.06 | 27.46 | 92.83 | |

Example 16

Following the above procedures, the partial recovery of acetic acid from a weak acid feed using a solvent mixture containing $P_{666,14}$-phosphinate, isopropyl acetate, and a residual amount of acetic acid was performed. The extraction was carried out at a solvent to feed ratio of 1.9 and an agitation of 95 SPM. Other conditions and the results are shown in Table 20.

TABLE 20

Partial Recovery of Acetic Acid with Solvent Mixture Containing $P_{666,14}$-phosphinate, Isopropyl Acetate, and Acetic Acid

| | Feed | Solvent | Raffinate | Extract | Component Mass Balance | Mass Balance |
|---|---|---|---|---|---|---|
| Flow Rate (g/min) | 8.68 | 16.44 | 4.38 | 20.57 | — | 99.3 |
| | | | | | | Acetic Acid Recovery (%) |
| Acetic Acid (wt %) | 34.23 | 1.68 | 1.08 | 14.47 | 93.09 | 100.2 |
| Water (wt %) | 64.46 | 2.42 | 97.08 | 7.83 | 97.75 | Ratio of Water/Acetic Acid (lb/lb) |
| Isopropyl Acetate (wt %) | 1.30 | 52.95 | 1.78 | 44.00 | 103.49 | 0.54 |
| $P_{666,14}$-phosphinate (wt %) | 0.00 | 42.94 | 0.06 | 33.70 | 98.24 | |

Example 17

Following the above procedures, the partial recovery of acetic acid from a weak acid feed using a solvent mixture containing $P_{666,14}$-phosphinate, isopropyl acetate, and a residual amount of acetic acid was performed. The extraction was carried out at a solvent to feed ratio of 0.91 and an agitation of 95 SPM. Other conditions and the results are shown in Table 21.

TABLE 21

Partial Recovery of Acetic Acid with Solvent Mixture Containing $P_{666,14}$-phosphinate, Isopropyl Acetate, and Acetic Acid

|  | Feed | Solvent | Raffinate | Extract | Component Mass Balance | Mass Balance |
|---|---|---|---|---|---|---|
| Flow Rate (g/min) | 13.09 | 11.89 | 6.89 | 16.86 | — | 95.1 |
|  |  |  |  |  |  | Acetic Acid Recovery (%) |
| Acetic Acid (wt %) | 34.23 | 1.68 | 4.83 | 22.60 | 88.52 | 85.04 |
| Water (wt %) | 64.46 | 2.42 | 92.76 | 11.30 | 95.12 | Ratio of Water/Acetic Acid (lb/lb) |
| Isopropyl Acetate (wt %) | 1.30 | 52.95 | 2.35 | 38.76 | 103.57 | 0.50 |
| $P_{666,14}$-phosphinate (wt %) | 0.00 | 42.94 | 0.06 | 27.34 | 90.36 |  |

Example 18

Following the above procedures, the partial recovery of acetic acid from a weak acid feed using a solvent mixture containing $P_{666,14}$-phosphinate and isopropyl acetate was performed. The extraction was carried out at a solvent to feed ratio of 1.9 and an agitation of 95 SPM. Other conditions and the results are shown in Table 22.

TABLE 22

Partial Recovery of Acetic Acid with Solvent Mixture Containing $P_{666,14}$-Phosphinate and Isopropyl Acetate

|  | Feed | Solvent | Raffinate | Extract | Component Mass Balance | Mass Balance |
|---|---|---|---|---|---|---|
| Flow Rate (g/min) | 8.68 | 16.44 | 7.20 | 17.71 | — | 99.1 |
|  |  |  |  |  |  | Acetic Acid Recovery (%) |
| Acetic Acid (wt %) | 3.40 | 1.63 | 1.13 | 2.46 | 91.72 | 147.66 |
| Water (wt %) | 94.46 | 1.75 | 96.76 | 7.15 | 96.97 | Ratio of Water/Acetic Acid (lb/lb) |
| Isopropyl Acetate (wt %) | 2.08 | 53.18 | 2.35 | 38.76 | 103.57 | 2.91 |
| $P_{666,14}$-phosphinate (wt %) | 0.07 | 43.44 | 0.08 | 40.94 | 101.53 |  |

Example 19

Following the above procedures, the partial recovery of acetic acid from a weak acid feed using a solvent mixture containing $P_{666,14}$-phosphinate, isopropyl acetate, and a residual amount of butyric acid was performed. The extraction was carried out at a solvent to feed ratio of 1.9 and an agitation of 95 SPM. Other conditions and the results are shown in Table 23.

TABLE 23

Partial Recovery of Acetic Acid with Solvent Mixture Containing $P_{666,14}$-phosphinate, Isopropyl Acetate, and Butyric Acid

| | Feed | Solvent | Raffinate | Extract | Component Mass Balance | Mass Balance |
|---|---|---|---|---|---|---|
| Flow Rate (g/min) | 8.68 | 16.44 | 7.14 | 17.13 | — | 99.1 |
| | | | | | | Acetic Acid Recovery (%) |
| Acetic Acid (wt %) | 3.47 | 0.00 | 0.00 | 1.72 | 97.73 | 97.73 |
| Butyric Acid (wt %) | 0.01 | 3.44 | 0.03 | 3.26 | 98.80 | |
| Water (wt %) | 93.03 | 1.32 | 94.43 | 6.16 | 94.06 | Ratio of Water/Acetic Acid (lb/lb) |
| Isopropyl Acetate (wt %) | 0.00 | 64.03 | 1.91 | 60.25 | 99.35 | 3.58 |
| $P_{666,14}$-phosphinate (wt %) | 0.02 | 43.69 | 0.02 | 36.07 | 86.05 | |

Procedures for Examples 20-23

Tie line data were measured for the extraction of lower carboxylic acids (formic acid, propionic acid, n-butyric acid, and acrylic acid) from water at both high (typically around 10-25 wt % of carboxylic acid in the organic phase) and low acid concentrations (typically around 1 to 5 wt % of acid in the organic phase) using three non-ionic solvents (MIBK, MTBE, and n-butyl acetate) and $P_{666,14}$-phosphinate at 40° C.

Roughly equal masses of water and solvent were added to a glass vial. The desired amount of carboxylic acid was added to the solvent-water mixture in amounts sufficient to yield either high or low acid concentration data. Once the acid was added, the mixture was agitated vigorously, and subsequently was allowed to separate into clear phases while maintaining the specified temperature. Each phase was sampled and analyzed by gas chromatography for water and carboxylic acid weight percent.

These data were used to calculate partition coefficients, with the controlling partition coefficient, $P_{cont}$, taken as the lesser of the partition coefficients at high and low acid concentrations. The data were also used to calculate the water to carboxylic acid weight ratio at high acid concentration, $R_{extr}$, and extraction factor, $\epsilon$.

Example 20

Extraction of Formic Acid with Non-Ionic Solvents and $P_{666,14}$-Phosphinate

Extraction factors for the extraction of formic acid with non-ionic solvents (MTBE, MIBK, and n-butyl acetate) and $P_{666,14}$-phosphinate were determined using the extraction procedure described above. Results are presented in Table 24.

TABLE 24

Extraction of Formic Acid with Non-Ionic Solvents and $P_{666,14}$-phosphinate at 40° C.

| Solvent | $P_{cont}$ | Formic Acid at $P_{cont}$ (wt %) | $R_{extr}$ | Extraction Factor ($\epsilon$) |
|---|---|---|---|---|
| MTBE | 0.68 | 16.8 | 0.69 | 1.0 |
| MIBK | 0.58 | 14.3 | 0.74 | 0.8 |
| BuOAc | 0.35 | 10.0 | 0.58 | 0.6 |
| $P_{666,14}$-phosphinate | 3.57 | 13.2 | 0.28 | 12.9 |

Example 21

Extraction of Propionic Acid with Non-Ionic Solvents and $P_{666,14}$-Phosphinate Extraction factors for the extraction of propionic acid with non-ionic solvents (MTBE, MIBK, and n-butyl acetate) and $P_{666,14}$-phosphinate were determined using the extraction procedure described above. Results are presented in Table 25.

TABLE 25

Extraction of Propionic Acid with Non-Ionic Solvents and $P_{666,14}$-phosphinate at 40° C.

| Solvent | $P_{cont}$ | Propionic Acid at $P_{cont}$ (wt %) | $R_{extr}$ | Extraction Factor ($\epsilon$) |
|---|---|---|---|---|
| MTBE | 3.2 | 20.2 | 0.30 | 10.7 |
| MIBK | 2.6 | 17.7 | 0.46 | 5.5 |
| BuOAc | 2.0 | 25.1 | 0.30 | 6.5 |
| $P_{666,14}$-phosphinate | 16.5 | 18.6 | 0.35 | 47.1 |

Example 22

Extraction of n-Butyric Acid with Non-Ionic Solvents and $P_{666,14}$-Phosphinate Extraction factors for the extraction of n-butyric acid with non-ionic solvents (MTBE, MIBK, and n-butyl acetate) and $P_{666,14}$-phosphinate were determined using the extraction procedure described above. Results are presented in Table 26.

TABLE 26

Extraction of n-Butyric Acid with Non-Ionic Solvents and $P_{666,14}$-phosphinate at 40° C.

| Solvent | $P_{cont}$ | n-Butyric Acid at $P_{cont}$ (wt %) | $R_{extr}$ | Extraction Factor ($\epsilon$) |
|---|---|---|---|---|
| MTBE | 9.9 | 25.2 | 0.20 | 48.5 |
| MIBK | 8.4 | 23.0 | 0.31 | 27.3 |
| BuOAc | 6.8 | 22.1 | 0.22 | 30.9 |
| $P_{666,14}$-phosphinate | 11.3 | 29.5 | 0.20 | 57.4 |

Example 23

Extraction of Acrylic Acid with Non-Ionic Solvents and $P_{666,14}$-Phosphinate Extraction factors for the extraction of acrylic acid with non-ionic solvents (MTBE, MIBK, and n-butyl acetate) and $P_{666,14}$-phosphinate were determined using the extraction procedure described above. Results are presented in Table 27.

TABLE 27

Extraction of Acrylic Acid with Non-Ionic Solvents and $P_{666,14}$-phosphinate at 40° C.

| Solvent | $P_{cont}$ | Acrylic Acid at $P_{cont}$ (wt %) | $R_{extr}$ | Extraction Factor ($\epsilon$) |
|---|---|---|---|---|
| MTBE | 3.6 | 24.2 | 0.31 | 11.8 |
| MIBK | 2.7 | 21.6 | 0.4 | 6.8 |
| BuOAc | 2.1 | 20.6 | 0.30 | 6.9 |
| $P_{666,14}$-phosphinate | 3.7 | 13.7 | 0.28 | 13.49 |

Example 24

Effect of Temperature on Extraction of Acetic Acid Using Non-Ionic Solvents

Tie line data were measured at 22 and 40° C. for each solvent listed in Table 28.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent.

These data were used to calculate partition coefficients, with the controlling partition coefficient, $P_{cont}$, taken as the lesser of the partition coefficients at high and low acid concentrations. The data were also used to calculate the water to carboxylic acid weight ratio at high acid concentration, $R_{extr}$, and extraction factor, $\epsilon$. Results are given in Table 28.

TABLE 28

Effect of Temperature on Acetic Acid Partitioning by Non-Ionic Solvents

| Solvent | T (° C.) | $P_{cont}$ | HOAc at $P_{cont}$ (wt %) | $R_{extr}$ | Extraction Factor ($\epsilon$) |
|---|---|---|---|---|---|
| MTBE | 22 | 0.9 | 2.0 | 0.5 | 1.88 |
| MTBE | 40 | 0.7 | 2.0 | 0.5 | 1.40 |
| MIBK | 22 | 0.67 | 3.9 | 1.14 | 0.59 |
| MIBK | 40 | 0.75 | 8.4 | 0.73 | 1.02 |
| i-PrOAc | 22 | 0.57 | 1.7 | 0.56 | 1.02 |
| i-PrOAc | 40 | 0.54 | 1.8 | 0.65 | 0.83 |

As seen from Table 28, the partition coefficient and extraction factor responds in different ways to changes in temperature in different NIO solvents.

Example 25

Effect of Temperature on Extraction of Acetic Acid Using $P_{666,14}$-Phosphinate Tie line data were measured at 20 and 40° C. for $P_{666,14}$-phosphinate.

Roughly equal masses of water and solvent were added to a glass vial. Acetic acid was added to the solvent-water mixture in amounts sufficient to yield either high or low acid concentration data. Once the acetic acid was added, the mixture was agitated vigorously, and subsequently was allowed to separate into clear phases while maintaining the specified temperature. Each phase was sampled and analyzed by gas chromatography for water and acetic acid weight percent.

These data were used to calculate partition coefficients, with the controlling partition coefficient, $P_{cont}$, taken as the lesser of the partition coefficients at high and low acid concentrations. The data were also used to calculate the water to carboxylic acid weight ratio at high acid concentration, $R_{extr}$, and extraction factor, $\epsilon$. Results are given in Table 29.

TABLE 29

Effect of Temperature on Extraction of Acetic Acid with $P_{666,14}$-phosphinate

| Temp. (° C.) | $P_{cont}$ | HOAc at $P_{cont}$ (wt %) | $R_{extr}$ | Extraction Factor ($\epsilon$) |
|---|---|---|---|---|
| 20 | 1.70 | 18.5 | 0.19 | 9.24 |
| 40 | 1.49 | 17.3 | 0.20 | 7.45 |

As seen from Table 29, the partition coefficient and extraction factor both decreased with increasing temperature for $P_{666,14}$-phosphinate.

The invention has been described in detail with particular reference to preferred embodiments thereof, but it will be understood that variations and modifications can be effected within the spirit and scope of the invention.

We claim:

1. A composition for separating a $C_1$ to $C_4$ carboxylic acid from water, the composition comprising:
    (a) a quaternary phosphonium phosphinate salt;
    (b) a co-solvent selected from the group consisting of higher carboxylic acids, ethers, esters, ketones, aromatic hydrocarbons, chlorinated hydrocarbons, and nitriles;
    (c) a $C_1$ to $C_4$ carboxylic acid; and
    (d) water,
    wherein the phosphinate salt has the general formula 1:

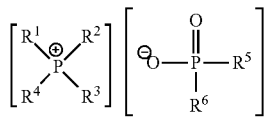

wherein
    $R^1$, $R^2$, $R^3$ and $R^4$ are each independently a $C_1$ to $C_{26}$ hydrocarbyl group, provided that $R^1$, $R^2$, $R^3$, and $R^4$ collectively have a total of at least 24 carbon atoms; and
    $R^5$ and $R^6$ are each independently an alkyl or aryl group having 3 to 24 carbon atoms and may be connected together with the phosphorus atom to form a heterocyclic ring.

2. The composition according to claim 1, wherein $R^5$ and $R^6$ are each independently an alkyl group having 6 to 12 carbon atoms.

3. The composition according to claim 2, wherein at least one of the alkyl groups represented by $R^5$ and $R^6$ is branched.

4. The composition according to claim 1, wherein the alkyl or aryl groups represented by $R^5$ and $R^6$ are the same.

5. The composition according to claim 1, wherein the phosphinate anion comprises bis(2,4,4-trimethylpentyl)phosphinate.

6. The composition according to claim 1, wherein the phosphinate salt comprises a trihexyl(tetradecyl)phosphonium cation.

7. The composition according to claim 1, which comprises at least two of the phosphinate salts.

8. The composition according to claim 1, wherein the co-solvent comprises a higher carboxylic acid.

9. The composition according to claim 8, wherein the higher carboxylic acid is selected from the group consisting of n-butyric acid, isobutyric acid, n-valeric acid, isovaleric acid, n-hexanoic acid, 2-ethylbutyric acid, heptanoic acid, n-octanoic, 2-ethylhexanoic acids, nonanoic acids, decanoic acids, dodecanoic acids, stearic acid, oleic acid, linolenic acid, and mixed vegetable-derived acids.

10. The composition according to claim 8, wherein the higher carboxylic acid is selected from the group consisting of benzoic acid, toluic acids, and 3-dimethylaminobenzoic acid.

11. The composition according to claim 1, wherein the co-solvent is selected from the group consisting of ethyl acetate, n-propyl acetate, n-propyl formate, i-propyl acetate, i-propyl formate, n-butyl acetate, n-butyl formate, i-butyl acetate, i-butyl formate, n-propyl propionate, i-propyl propionate, 2-pentanone, 3-pentanone, methyl isobutyl ketone, 3-methyl-2-butanone, 2-hexanone, 2-heptanone, cyclohexanone, 4-methyl-2-pentanone, 2,4-dimethyl-3-pentanone, 5-methyl-2-hexanone, 4-heptanone, 2-octanone, 5-nonanone, 2,8-dimethyl-4-heptanone, 3,3,5-trimethyl cyclohexanone, isophorone, diethyl ether, methyl propyl ether, dipropyl ether, di-isopropyl ether, methyl t-butyl ether, tertiary amyl methyl ether, ethyl butyl ether, toluene, m-xylene, p-xylene, and o-xylene.

12. The composition according to claim 1, wherein the co-solvent is selected from the group consisting of methyl isobutyl ketone, toluene, isopropyl acetate, and methyl t-butyl ether.

13. The composition according to claim 1, which comprises at least two of the co-solvents.

14. The composition according to claim 1, which comprises 5 to 95 weight percent of the phosphinate salt and 5 to 95 weight percent of the co-solvent.

15. The composition according to claim 1, which comprises 50 to 90 weight percent of the phosphinate salt and 10 to 50 weight percent of the co-solvent.

16. A process for separating a $C_1$ to $C_4$ carboxylic acid from water, the process comprising:
    contacting a feed mixture comprising a $C_1$ to $C_4$ carboxylic acid and water with an extraction solvent comprising a quaternary phosphonium phosphinate salt and a co-solvent at conditions effective to form (a) an extract mixture comprising the phosphinate salt, the co-solvent, and at least a portion of the $C_1$ to $C_4$ carboxylic acid from the feed mixture and (b) a raffinate mixture comprising water and less of the $C_1$ to $C_4$ carboxylic acid compared to the feed mixture,
    wherein the co-solvent is selected from the group consisting of higher carboxylic acids, ethers, esters, ketones, aromatic hydrocarbons, chlorinated hydrocarbons, and nitriles; and
    wherein the phosphinate salt has the general formula 1:

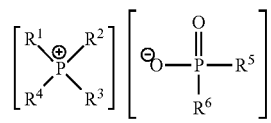

wherein
    $R^1$, $R^2$, $R^3$ and $R^4$ are each independently a $C_1$ to $C_{26}$ hydrocarbyl group, provided that $R^1$, $R^2$, $R^3$, and $R^4$ collectively have a total of at least 24 carbon atoms; and
    $R^5$ and $R^6$ are each independently an alkyl or aryl group having 3 to 24 carbon atoms and may be connected together with the phosphorus atom to form a heterocyclic ring.

17. The process according to claim 16, wherein the phosphinate anion comprises bis(2,4,4-trimethylpentyl)phosphinate.

18. The process according to claim 16, wherein the phosphinate salt comprises a trihexyl(tetradecyl)phosphonium cation.

19. The process according to claim 16, wherein the extraction solvent comprises at least two of the phosphinate salts.

20. The process according to claim 16, wherein the higher carboxylic acid is selected from the group consisting of n-butyric acid, isobutyric acid, n-valeric acid, isovaleric acid, n-hexanoic acid, 2-ethylbutyric acid, heptanoic acid, n-octanoic, 2-ethylhexanoic acids, nonanoic acids, decanoic acids, dodecanoic acids, stearic acid, oleic acid, linolenic acid, and mixed vegetable-derived acids.

21. The process according to claim 20, wherein the higher carboxylic acid is selected from the group consisting of benzoic acid, toluic acids, and 3-(dimethylamino)benzoic acid.

22. The process according to claim 16, wherein the co-solvent is selected from the group consisting of ethyl acetate, n-propyl acetate, n-propyl formate, i-propyl acetate, i-propyl formate, n-butyl acetate, n-butyl formate, i-butyl acetate, i-butyl formate, n-propyl propionate, i-propyl propionate, 2-pentanone, 3-pentanone, methyl isobutyl ketone, 3-methyl-2-butanone, 2-hexanone, 2-heptanone, cyclohexanone, 4-methyl-2-pentanone, 2,4-dimethyl-3-pentanone, 5-methyl-2-hexanone, 4-heptanone, 2-octanone, 5-nonanone, 2,8-dimethyl-4-heptanone, 3,3,5-trimethyl cyclohexanone, isophorone, diethyl ether, methyl propyl ether, dipropyl ether, di-isopropyl ether, methyl t-butyl ether, tertiary amyl methyl ether, ethyl butyl ether, toluene, m-xylene, p-xylene, and o-xylene.

23. The process according to claim 16, wherein the extraction solvent comprises at least two of the co-solvents.

24. The process according to claim 16, wherein the $C_1$ to $C_4$ carboxylic acid is selected from the group consisting of formic acid, acetic acid, propionic acid, acrylic acid, n-butyric acid, isobutyric acid, methacrylic acid, and trifluoroacetic acid.

25. The process according to claim 16, wherein the $C_1$ to $C_4$ carboxylic acid comprises acetic acid.

26. The process according to claim 16, wherein the feed mixture comprises at least two of the $C_1$ to $C_4$ carboxylic acids.

27. The process according to claim 16, wherein the feed mixture comprises 0.5 to 60 weight percent of the $C_1$ to $C_4$ carboxylic acid.

28. The process according to claim 16, wherein the feed mixture is derived from the production of cellulose esters.

29. The process according to claim 16, wherein the weight ratio of the extraction solvent to the feed mixture ranges from 0.2 to 10:1.

30. The process according to claim 16, which further comprises:
    separating the extract mixture from the raffinate mixture; and
    recovering the $C_1$ to $C_4$ carboxylic acid from the extract mixture by distillation at atmospheric pressure or lower.

* * * * *